United States Patent
Carven et al.

(10) Patent No.: US 12,281,159 B2
(45) Date of Patent: Apr. 22, 2025

(54) TGFβ ANTIBODIES, METHODS AND USES

(71) Applicant: Scholar Rock, Inc., Cambridge, MA (US)

(72) Inventors: Gregory J. Carven, Maynard, MA (US); Thomas Schurpf, Cambridge, MA (US); Katherine Turner, Acton, MA (US)

(73) Assignee: Scholar Rock, Inc., Cambridge, MA (US)

( * ) Notice: Subject to any disclaimer, the term of this patent is extended or adjusted under 35 U.S.C. 154(b) by 890 days.

(21) Appl. No.: 17/329,859

(22) Filed: May 25, 2021

(65) Prior Publication Data

US 2021/0277100 A1 Sep. 9, 2021

Related U.S. Application Data

(63) Continuation of application No. 16/317,635, filed as application No. PCT/US2017/042162 on Jul. 14, 2017, now abandoned.

(60) Provisional application No. 62/371,355, filed on Aug. 5, 2016, provisional application No. 62/362,393, filed on Jul. 14, 2016.

(51) Int. Cl.

| | | |
|---|---|---|
| *C07K 16/22* | (2006.01) | |
| *A61K 38/18* | (2006.01) | |
| *A61K 39/00* | (2006.01) | |
| *A61K 39/39* | (2006.01) | |
| *A61K 39/395* | (2006.01) | |
| *C07K 16/28* | (2006.01) | |
| *C12N 9/00* | (2006.01) | |

(52) U.S. Cl.
CPC ............. *C07K 16/22* (2013.01); *A61K 38/18* (2013.01); *A61K 39/39* (2013.01); *A61K 39/3955* (2013.01); *C07K 16/28* (2013.01); *C12N 9/00* (2013.01); *A61K 2039/505* (2013.01); *C07K 2317/32* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,728,813 | A | 3/1998 | Lyman et al. |
| 5,747,498 | A | 5/1998 | Schnur et al. |
| 5,969,110 | A | 10/1999 | Beckmann et al. |
| 5,981,245 | A | 11/1999 | Fox et al. |
| 6,057,124 | A | 5/2000 | Bartley et al. |
| 6,232,447 | B1 | 5/2001 | Cerretti |
| 6,413,932 | B1 | 7/2002 | Cerretti et al. |
| 6,479,635 | B1 | 11/2002 | Anderson et al. |
| 6,521,424 | B2 | 2/2003 | Cerretti et al. |
| 6,596,852 | B2 | 7/2003 | Cerretti et al. |
| 6,737,056 | B1 | 5/2004 | Presta |
| 6,740,511 | B1 | 5/2004 | Van Raaij et al. |
| 7,067,475 | B2 | 6/2006 | Cerretti et al. |
| 7,074,408 | B2 | 7/2006 | Fanslow, III et al. |
| 2002/0039992 | A1 | 4/2002 | Cerretti et al. |
| 2002/0042368 | A1 | 4/2002 | Fanslow, III et al. |
| 2002/0103358 | A1 | 8/2002 | Cerretti et al. |
| 2003/0059937 | A1* | 3/2003 | Ruben ............... A61P 35/00 530/391.1 |
| 2003/0162712 | A1 | 8/2003 | Cerretti et al. |
| 2006/0246071 | A1 | 11/2006 | Green et al. |
| 2008/0219979 | A1 | 9/2008 | Tocker et al. |
| 2011/0189082 | A1 | 8/2011 | Kirchner et al. |

FOREIGN PATENT DOCUMENTS

| | | |
|---|---|---|
| WO | WO 95/19970 A1 | 7/1995 |
| WO | WO 98/02434 A1 | 1/1998 |
| WO | WO 98/14451 A1 | 4/1998 |
| WO | WO 03/002713 A2 | 1/2003 |
| WO | WO 03/086289 A2 | 10/2003 |
| WO | WO 2007/014162 A2 | 2/2007 |
| WO | WO 2014/055648 A1 | 4/2014 |
| WO | WO 2014/182676 A2 | 11/2014 |
| WO | WO 2015/015003 A1 | 2/2015 |
| WO | WO 2015/171691 A2 | 11/2015 |
| WO | WO 2017/156500 A1 | 9/2017 |

OTHER PUBLICATIONS

GenBank Accession AFR33667.1, 2012, pp. 1-2.*
Masuda, 2006, FEBS Journal, pp. 2184-2194.*
UniProtKB Accession P011861.1, 2010, pp. 1-6.*
Hall, 1992, J. Immunol. Vol. 149: 1605-1612.*
Rabia et al. 2018, Biochem. Eng. J. Vol. 137: 365-374.*
Chothia, et al., "Conformations of immunoglobulin hypervariable regions," Nature, 342: 877-883 (1989).
Chothia, et al., "Canonical Structures for the Hypervariable Regions of Immunoglobulins," Journal of Molecular Biology, 196: 901-917 (1987).
Martin J. Cline, "Perspectives for Gene Therapy: Inserting New Genetic Information into Mammalian Cells by Physical Techniques and Viral Vectors," Pharmaceutical Therapies: 29: 69-092 (1985).

(Continued)

Primary Examiner — Amy E Juedes
(74) Attorney, Agent, or Firm — FINNEGAN, HENDERSON, FARABOW, GARRETT & DUNNER, LLP

(57) ABSTRACT

ProTGFβ1-GARP complex-selective antibodies, polynucleotides capable of encoding the proTGFβ1-GARP complex-selective antibodies or antigen-binding fragments, cells expressing proTGFβ1-GARP complex-selective antibodies or antigen-binding fragments, as well as associated vectors and detectably labeled proTGFβ1-GARP complex-selective antibodies or antigen-binding fragments may be used to enhance an immune response in a subject, for example, against a cancer.

26 Claims, 4 Drawing Sheets
Specification includes a Sequence Listing.

(56) References Cited

OTHER PUBLICATIONS

Colombo, et al., Regulatory T-cell inhibition versus depletion: the right choice in cancer immunotherapy, Nature, 7: 880-887 (2007).
Cuende, et al., "Monoclonal Antibodies Against GARP/TFG-β1 Complexes Inhibit the Immunosuppressive Activity of Human Regulatory T Cells in Vivo," Science Translational Medicine, 7 (284): 1-13 (2015).
Derynck, et al., "Human transforming growth factor-β complementary DNA sequence and expression in normal and transformed cells," Nature, 316: 701-705 (1985).
Ferrara, et al., "The Carbohydrate at FCγRIIIa Asn-162," The Journal of Biological Chemistry, 281 (8): 5032-5036 (2006).
Ferrera, et al., "Modulation of Therapeutic Antibody Effector Functions by Glycosylation Engineering: Influence of Golgi Enzyme Localization Domain and Co-Expression of Heterologous β1, 4-N-acetylglucosaminyltransferase III and Golgi α-mannosidase II," Biotechnology and Bioengineering, 93 (5): 851-861 (2006).
Gadi, et al., "In vivo sensitization of ovarian tumors to chemotherapy by expression of E. coli purine nucleoside phosphorylase in a small fraction of cells," Gene Therapy, 7: 1738-1743 (2000).
Holt, et al, "Domain antibodies: proteins for therapy," TRENDS in Biotechnology, 21 (11): 484-490 (2003).
Konno, et al., "Fucose content of monoclonal antibodies can be controlled by culture medium osmolality for high antibody-dependent cellular cytotoxicity," Cytotechnology, 64: 249-265 (2012).
Lienart, et al., "Structural basis of latent TGF-b1 presentation and activation by GARP on human regulatory T cells," Science, 362 (6417): 952-956 (2018).
Lonning, et al., "Antibody Targeting of TGF-β in Cancer Patients," Current Pharmaceutical Biotechnology, 12: 2176-2189 (2011).
Maccallum, et al., "Antibody-antigen Interaction: Contact Analysis and Binding Site Topography," Journal of Molecular Biology, 262: 732-745 (1996).
Martin, et al., "Structural Families in Loops of Homologous Proteins: Automatic Classification, Modelling and Application to Antibodies," Journal of Molecular Biology, 263: 800-815 (1996).
Mori, et al., "Engineering Chinese Hamster Ovary Cells to Maximize Effector Function of Produced Antibodies Using FUT8 siRNA," Biotechnology and Bioengineering, 88 (7): 901-908 (2004).
Myers, et al., "Optimal alignments in linear space," CABIOS, 4 (1): 11-17 (1988).
Needleman, et al., "A General Method Applicable to the Search for Similarities in the Amino Acid Sequence of Two Proteins," Journal of Molecular Biology, 48: 443-453 (1970).
Okayama, et al., "A cDNA Cloning Vector That Permits Expression of cDNA Inserts in Mammalian Cells," Molecular and Cellular Biology, 3 (2): 280-289 (1983).
Olivier, et al., "EB66 cell line, a duck embryonic stem cell-derived substrate for the industrial production of therapeutic monoclonal antibodies with enhanced ADCC activity," mAbs, 2 (4): 405-415 (2010).
Rivets, et al., "Nanobodies as novel agents for cancer therapy," Expert Opinion on Biological Therapy, 5 (1): 111-124 (2005).
Shields, et al., "Lack of Fucose on Human IgG1 N-Linked Oligosaccharide Improves Binding to Human FcγRIII and Antibody-dependent Cellular Toxicity," The Journal of Biological Chemistry, 277 (30): 26733-26740 (2002).
Shinkawa, et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," The Journal of Biological Chemistry, 278 (5): 3466-3473 (2003).
Stockis, et al., "Comparison of stable human Treg and Th clones by transcriptional profiling," European Journal of Immunology, 39: 869-882 (2009).
Sun, et al., "GARP: a surface molecule of regulatory T cells that is involved in the regulatory function and TGF-[beta] releasing," Oncotarget, 7 (27): 42826-42836 (2016).
Tran, et al., "GARP (LRRC32) is Essential for the Surface Expression of Latent TGF-β on Platelets and Activated FOXP3+ Regulatory T Cells," Proceedings of the National Academy of Sciences, 106: 3445-3450 (2009).
Ward, et al., "Binding activities of a repertoire of single immunoglobulin variable domains secreted from *Escherichia coli*," Nature, 341: 544-546 (1989).
Zhou, et al., "Development of a Simple and Rapid Method for Producing Non-Fucosylated Oligomannose Containing Antibodies With Increased Effector Function," Biotechnology and Bioengineering, 99 (3): 652-665 (2008).
PCT International Search Report dated Oct. 20, 2017.
Supplementary European Search Report dated Apr. 3, 2020.

\* cited by examiner

* $p < 0.01$ when compared to IgG control + $T_{regs}$ using Dunnett's 1-way ANOVA

Figure 4

| Clone | Affinity K$_D$ (nM) | | | | | | | | | |
|---|---|---|---|---|---|---|---|---|---|---|
| | hGARP-proTGFβ1 | hGARP-TGFβ1-LAP | mGARP-proTGFβ1 | rGARP-proTGFβ1 | hLTBP1-proTGFβ1 | hLTBP3-proTGFβ1 | TGFβ1 | TGFβ2 | TGFβ3 | hLRRC3-pro-TGFβ1 |
| 4B1C1 | 0.114±0.004 | 11.3±1.2 | No binding | 0.187±0.007 | No binding | No binding | No binding | No binding | No binding | |
| 4B16B9 | 0.002±0.03 | No binding | No binding | 0.158±0.012 | No binding | No binding | No binding | No binding | No binding | |

TGFβ ANTIBODIES, METHODS AND USES

CROSS-REFERENCE TO RELATED APPLICATIONS

This application is a Continuation of U.S. application Ser. No. 16/317,635, filed 14 Jan. 2019, currently pending, which is a 371 national stage Application of International Application Number PCT/US2017/042162, filed 14 Jul. 2017, which claims the benefit of U.S. Provisional Application Ser. No. 62/362,393, filed 14 Jul. 2016 and U.S. Provisional Application Ser. No. 62/371,355, filed 5 Aug. 2016. The entire content of the aforementioned applications is incorporated herein by reference in its entirety.

SEQUENCE LISTING

The instant application contains a Sequence Listing which has been submitted electronically in ASCII format and is hereby incorporated by reference in its entirety. Said ASCII copy, created on 18 May 2021, is named JBI5093USCNT1.txt and is 28 kilobytes in size.

TECHNICAL FIELD

The present invention relates to monoclonal antibodies that inhibit growth factor activity and methods of producing and using the described antibodies.

BACKGROUND

Regulatory T cells, or Tregs, are a subset of CD4+T lymphocytes specialized in the inhibition of immune responses. Insufficient Treg function results in autoimmune pathology, while excessive Treg function may inhibit anti-tumor immune responses in cancer patients. The exact mechanisms by which Tregs inhibit immune responses are not fully understood. Due to their immunosuppressive functions, Tregs represent potential inhibitors of spontaneous or vaccine-induced anti-tumor immune responses. In murine models, the depletion of Tregs can improve immune responses against experimental tumors (Colombo et al. Nat. Rev. Cancer 2007, 7:880-887). Thus, targeting Tregs in humans could improve the efficacy of immunotherapy against cancer.

TGF-β1, which is instrumental in activating human Tregs but not other types of human T lymphocytes (Stockis, J. et al. Eur. J. Immunol. 2009, 39:869-882), could be a target of interest. However, antibodies against hTGF-β1 were not found promising. Phase 1 clinical trials have been conducted in focal segmental glomerulosclerosis (FSGS), idiopathic pulmonary fibrosis (IPF) and advanced malignant melanoma or renal cell carcinoma (RCC) (Lonning S et al. Current Pharmaceutical Biotechnology 2011, 12:2176-2189). Depending on the trial, adverse events were observed in some patients. The main adverse reactions reported consisted in the development of keratoacanthoma (KA) and squamous cell carcinoma (SCC) in melanoma patients. It is possible that KA or SCC lesions in melanoma patients evolved from pre-cancerous cells whose proliferation was being inhibited by endogenous TGF-β1 (Lonning S et al. Current Pharmaceutical Biotechnology 2011, 12:2176-2189). Therefore, a major concern regarding the use of anti-TGF-β1 antibodies in the context of cancer is that they may favor the appearance of new neoplastic lesions, due to the inhibition of the tumor-suppressive effect exerted by endogenous TGF-β1 on pre-cancerous cells. Thus, new strategies for improving cancer treatment by preventing TGF-β1 release from Tregs are desirable.

SUMMARY OF THE PRESENT INVENTION

The present invention includes proTGFβ1-GARP complex-selective antibodies and antigen-binding fragments thereof. Also described are related polynucleotides capable of encoding the provided proTGFβ1-GARP complex-selective antibodies and antigen-binding fragments, cells expressing the provided antibodies and antigen-binding fragments, as well as associated vectors and detectably labeled proTGFβ1-GARP complex-selective antibodies and antigen-binding fragments. The antibody or antigen binding fragment thereof does not selectively bind to a TGFβ1 growth factor domain, a TGFβ2 growth factor domain, a TGFβ3 growth factor domain, proTGFβ1 covalently associated with LTBP1, proTGFβ1 covalently associated with LTBP3, proTGFβ1 covalently associated with LRRC33, and proTGFβ1 that is unassociated with human GARP, as measured by OctetRed_384 under the conditions shown in Examples 4-6.

In some embodiments, the antibodies and antigen-binding fragments of the invention may have: (1) a dissociation constant (Kd) of less than or equal to 1 nM for human proTGFβ1 in a complex with human glycoprotein A repetitions predominant (proTGFβ1-GARP complex) in solution; (2) an inhibitory concentration (IC50) of less than or equal to 10 nM for inhibition of TGFβ1 growth factor release from cell-associated proTGFβ1-GARP complex; and (3) a greater than 100-fold selectivity for proTGFβ1-GARP complex over TGFβ1 growth factor domain, TGFβ2 growth factor domain, TGFβ3 growth factor domain, proTGFβ1 covalently associated with LTBP1, proTGFβ1 covalently associated with LTBP3, and proTGFβ1 covalently associated with LRRC33, wherein the isolated antibodies, or antigen binding fragments thereof, do not bind to proTGFβ1 that is unassociated with human GARP.

In addition, methods of using the provided proTGFβ1-GARP complex-selective antibodies and antigen-binding fragments are described. The described proTGFβ1-GARP complex-selective antibodies can be used in methods of treating a variety of TGFβ1-related diseases or disorders in which it is desirable to modulate an immune response, such as a variety of immunotherapy applications, e.g., cancers, vaccines and infectious disease.

In some embodiments, the present invention comprises isolated antibodies and antigen-binding fragments wherein the antibody or antigen binding fragment specifically binds to human proTGFβ1 in a complex with human glycoprotein A repetitions predominant (proTGFβ1-GARP complex) while said complex is in solution. These proTGFβ1-GARP complex-selective antibodies, or antigen-binding fragments thereof may inhibit Treg function in vitro. In some embodiments, the proTGFβ1-GARP complex-selective antibodies and antigen-binding fragments inhibit activation of TGFβ1. In some embodiments the proTGFβ1-GARP complex-selective antibodies and antigen-binding fragments bind to an epitope of human proTGFβ1 modified as a result of complex formation with human GARP. This proTGFβ1-GARP complex-selective antibody or antigen-binding fragment may bind to proTGFβ1 of a proTGFβ1-GARP complex with a binding affinity of 880 pM or less.

TABLE 1

CDR sequences of human proTGFβ-GARP complex-selective mAbs

| ID | HC-CDR1 | HC-CDR2 | HC-CDR3 | LC-CDR1 | LC-CDR2 | LC-CDR3 |
|---|---|---|---|---|---|---|
| 4B1C1 | DYTMH (4) | LISWDGGSTYYADSVKG (5) | DADDSTFDI (6) | RASQSVSRNLA (7) | WASTRES (8) | QQYYSVPYT (9) |
| 4B16B9 | SYAIS (10) | GIIPMFGTTNYAQKFQG (11) | DREWEPAYGMDV (12) | IGTSSDVGGYNYVS (13) | DVSNRPS (14) | SAYTVSSTWV (15) |

(SEQ ID NO:)

In some embodiments, the proTGFβ1-GARP complex-selective antibody, or an antigen-binding fragment thereof, comprises a heavy chain comprising a CDR1, a CDR2, and a CDR3 of any one of the amino acid sequences described in Table 1 and a light chain comprising a CDR1, a CDR2, and a CDR3 of any one of the amino acid sequences described in Table 1. The proTGFβ1-GARP complex-selective antibodies of the invention may comprise the heavy chain variable regions sequences of SEQ ID NOs: 16 and 18 and may comprise the light chain variable region sequences of SEQ ID NOs 17 and 19.

The proTGFβ1-GARP complex-selective antibodies described herein include antibodies with the described features of the CDRs and variable domains in combination with any of the IgG isotypes, including modified versions in which the Fc sequence has been modified to effect different effector functions.

In addition to the described proTGFβ1-GARP complex-selective antibodies and antigen-binding fragments, also provided are polynucleotide sequences capable of encoding the proTGFβ1-GARP complex-selective antibodies and antigen-binding fragments. Vectors comprising the described polynucleotides are also provided, as are cells expressing the proTGFβ1-GARP complex-selective antibodies or antigen-binding fragments provided herein. Also described are cells capable of expressing the disclosed vectors. These cells may be mammalian cells (such as 293F cells, CHO cells), insect cells (such as Sf9 cells), yeast cells, plant cells, or bacteria cells (such as E. coli). A process for the production of the proTGFβ1-GARP complex-selective antibodies or antigen-binding fragments is also provided.

The present invention also comprises methods of using the proTGFβ1-GARP complex-selective antibodies or antigen-binding fragments. ProTGFβ1-GARP complex-selective antibodies for use in the methods discussed in this section include those with the set of CDRs described for antibodies in Table 1. For example, the key role that TGFβ1 plays in an immune response makes it an attractive target for immunotherapy, including inducing or enhancing an immune response against any weakly immunogenic antigen including tumor antigens. As such, the proTGFβ1-GARP complex-selective antibodies have utility in the treatment of various cancers and infectious disease.

In one embodiment, the proTGFβ1-GARP complex-selective antibodies are administered to block the release of TGFβ1 from Tregs and thereby, prevent the inhibition of effector T cell activity by regulatory T cells. Such inhibition can be assayed by a variety of methods known in the art, including, for example, by monitoring T cell proliferation, expression of known markers of activation, or cytokine secretion. In another embodiment, a proTGFβ1-GARP complex-selective antibody is administered to a subject to decrease the level of regulatory T cells, for instance the level of tumor regulatory T cells. In yet another embodiment, the activity of effector T cells is induced or enhanced by administering a proTGFβ1-GARP complex-selective antibody as provided herein.

Within the scope of the invention are kits including the disclosed proTGFβ1-GARP complex-selective antibodies or antigen-binding fragments thereof. The described kits may be used to carry out the methods of using the proTGFβ1-GARP complex-selective antibodies or antigen-binding fragments provided herein, or other methods known to those skilled in the art. In some embodiments the described kits may include the proTGFβ1-GARP complex-selective antibodies or antigen-binding fragments described herein and reagents for use in detecting the presence of proTGFβ1-GARP complex in a biological sample and, optionally, a vessel for containing the proTGFβ1-GARP complex-selective antibody or fragment when not in use, instructions for use of the proTGFβ1-GARP complex-selective antibody or fragment, the proTGFβ1-GARP complex-selective antibody or fragment affixed to a solid support, and/or detectably labeled forms of the proTGFβ1-GARP complex-selective antibody or fragment.

BRIEF DESCRIPTION OF THE DRAWINGS

FIG. 4. Octet affinity results for proTGFβ1-GARP complex-selective antibody candidates demonstrate specificity by binding to the human proTGFβ1-GARP complex but no other proTGFb1-complexes or soluble forms of TGFb1, 2 or 3.

DETAILED DESCRIPTION OF ILLUSTRATIVE EMBODIMENTS

Definitions

Figure 1:
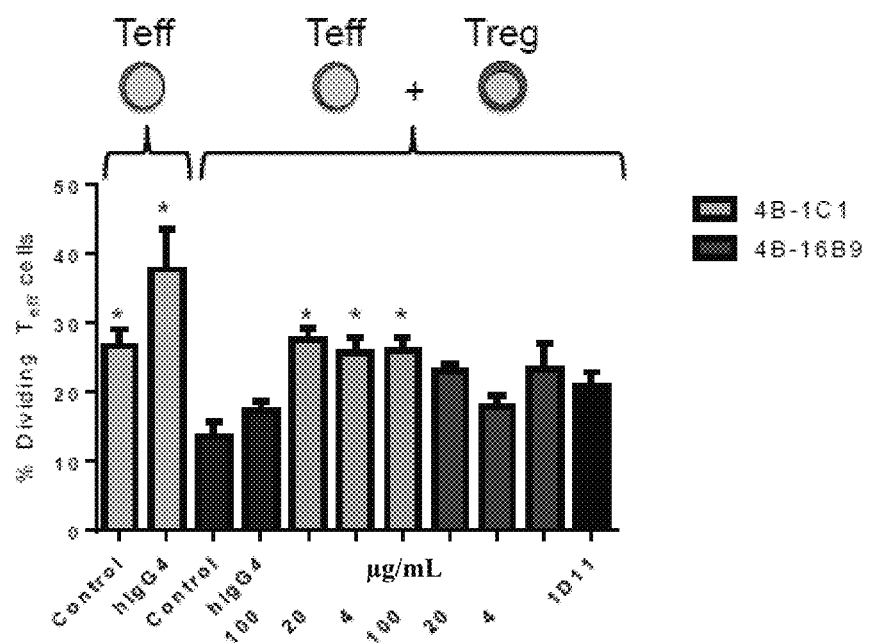
FIG. 1 shows that addition of 4B1C1 and 4B16B9 to T cell co-cultures inhibit T regulatory cell activity through the enhanced growth of T effector cells.
Figure 2:
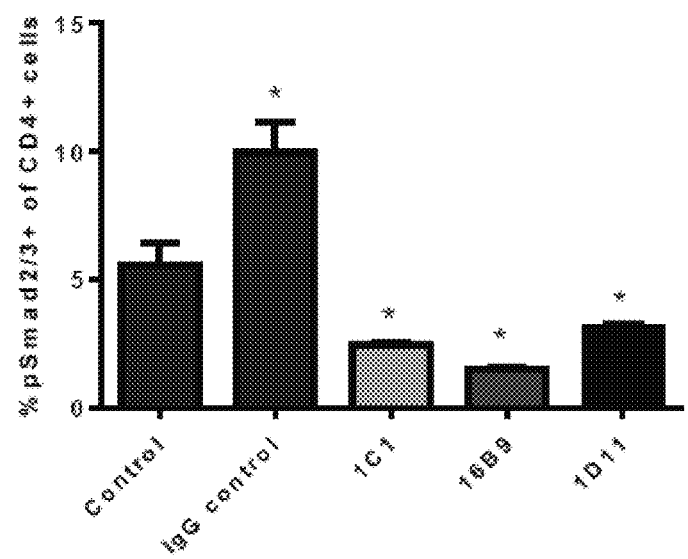
FIG. 2 shows 4B1C1 and 4B16B9 inhibit TGFβ1 activation as assessed by SMAD signaling.

Various terms relating to aspects of the description are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of up to ±10% from the specified value, as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

"Isolated" means a biological component (such as a nucleic acid, peptide or protein) has been substantially separated, produced apart from, or purified away from other biological components of the organism in which the component naturally occurs, i.e., other chromosomal and extra-chromosomal DNA and RNA, and proteins. Nucleic acids, peptides and proteins that have been "isolated" thus include nucleic acids and proteins purified by standard purification methods. "Isolated" nucleic acids, peptides and proteins can be part of a composition and still be isolated if such composition is not part of the native environment of the nucleic acid, peptide, or protein. The term also embraces nucleic acids, peptides and proteins prepared by recombinant expression in a host cell as well as chemically synthesized nucleic acids. An "isolated" antibody or antigen-binding fragment, as used herein, is intended to refer to an antibody or antigen-binding fragment which is substantially free of other antibodies or antigen-binding fragments having different antigenic specificities (for instance, an isolated antibody that is a proTGFβ1-GARP complex-selective antibody is substantially free of antibodies that are not proTGFβ1-GARP complex-selective antibodies).

As used herein, the terms "transforming growth factor beta-1" and "TGFβ1" specifically include the human TGFβ1 protein. TGFβ1 is also known in the scientific literature as TGFbeta1 and TGFβ1. TGFβ1 growth factor is synthesized in conjunction with a prodomain, for example as described in GenBank™ Accession No. AK291907, NCBI Reference Sequence: NP_000651.3.1 and UniProtKB/Swiss-Prot Accession No. P01137.2 (see also Derynck et al. 1985, Nature 316, 701-705). In a particular embodiment, the TGFβ1 translated protein is a human protein having the amino acid sequence of SEQ ID NO: 2. TGFβ1 that includes both prodomain and growth factor elements is referred to herein as "proTGFβ1." In some embodiments, proTGFβ1 includes prodomain and growth factor components that have been proteolytically separated, but that remain associated through one or more chemical interactions. Such chemical interactions may include, but are not limited to, hydrophobic bonds, interactions influenced by van der Waals forces, polar and ionic interactions, hydrogen bonds, and noncovalent bonds.

As used herein, the terms "glycoprotein A repetitions predominant" and "GARP" refer to human GARP. GARP is otherwise known as leucine-rich repeat-containing protein 32 (LRRC32) and garpin. NCBI Reference Sequence NP_001122394.1 and NP_005503.1 provide exemplary human GARP amino acid sequences. In a particular embodiment, the GARP is a human GARP of SEQ ID NO: 1.

"Antibody" refers to all isotypes of immunoglobulins (IgG, IgA, IgE, IgM, IgD, and IgY) including various monomeric, polymeric and chimeric forms, unless otherwise specified. Specifically encompassed by the term "antibody" are polyclonal antibodies, monoclonal antibodies (mAbs), and antibody-like polypeptides, such as chimeric antibodies and humanized antibodies.

"Antigen-binding fragments" are any proteinaceous structure that may exhibit binding affinity for a particular antigen. Antigen-binding fragments include those provided by any known technique, such as enzymatic cleavage, peptide synthesis, and recombinant techniques. Some antigen-binding fragments are composed of portions of intact antibodies that retain antigen-binding specificity of the parent antibody molecule. For example, antigen-binding fragments may comprise at least one variable region (either a heavy chain or light chain variable region) or one or more CDRs of an antibody known to bind a particular antigen. Examples of suitable antigen-binding fragments include, without limitation diabodies and single-chain molecules as well as Fab, F(ab')2, Fc, Fabc, and Fv molecules, single chain (Sc) antibodies, individual antibody light chains, individual antibody heavy chains, chimeric fusions between antibody chains or CDRs and other proteins, protein scaffolds, heavy chain monomers or dimers, light chain monomers or dimers, dimers consisting of one heavy and one light chain, a monovalent fragment consisting of the VL, VH, CL and CH1 domains, or a monovalent antibody as described in WO2007059782, bivalent fragments comprising two Fab fragments linked by a disulfide bridge at the hinge region, a Fd fragment consisting essentially of the V.sub.H and C.sub.H1 domains; a Fv fragment consisting essentially of the VL and VH domains of a single arm of an antibody, a dAb fragment (Ward et al., Nature 341, 544-546 (1989)), which consists essentially of a VH domain and also called domain antibodies (Holt et al; Trends Biotechnol. 2003 November; 21(11):484-90); camelid or nanobodies (Revets et al; Expert Opin Biol Ther. 2005 January; 5(1):111-24); an isolated complementarity determining region (CDR), and the like. All antibody isotypes may be used to produce antigen-binding fragments. Additionally, antigen-binding fragments may include non-antibody proteinaceous frameworks that may successfully incorporate polypeptide segments in an orientation that confers affinity for a given antigen of interest, such as protein scaffolds. Antigen-binding fragments may be recombinantly produced or produced by enzymatic or chemical cleavage of intact antibodies. The phrase "an antibody or antigen-binding fragment thereof" may be used to denote that a given antigen-binding fragment incorporates one or more amino acid segments of the antibody referred to in the phrase.

The terms "CDR", and its plural "CDRs", refer to a complementarity determining region (CDR) of which three make up the binding character of a light chain variable region (CDRL1, CDRL2 and CDRL3) and three make up the binding character of a heavy chain variable region (CDRH1, CDRH2 and CDRH3). CDRs contribute to the functional activity of an antibody molecule and are separated by amino acid sequences that comprise scaffolding or framework regions. The exact definitional CDR boundaries and lengths are subject to different classification and numbering systems. CDRs may therefore be referred to by Kabat, Chothia, contact or any other boundary definitions. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat et al., *Sequences of Proteins of Immunological Interest*, 5th ed. NIH Publication No. 91-3242 (1991); Chothia et al., "Canonical Structures For the Hypervariable Regions of Immunoglobulins," *J. Mol. Biol.* 196:901 (1987); and MacCallum et al., "Antibody-Antigen Interactions: Contact Analysis and Binding Site Topography," J. Mol. Biol. 262:732 (1996)), each of which is hereby incorporated by reference in its entirety.

Typically, CDRs form a loop structure that can be classified as a canonical structure. The term "canonical structure" refers to the main chain conformation that is adopted by the antigen binding (CDR) loops. From comparative structural studies, it has been found that five of the six antigen binding loops have only a limited repertoire of available conformations. Each canonical structure can be characterized by the torsion angles of the polypeptide backbone. Correspondent loops between antibodies may, therefore, have very similar three dimensional structures, despite high amino acid sequence variability in most parts of the loops (Chothia et al., "Canonical Structures For the Hypervariable Regions of Immunoglobulins," *J. Mol. Biol.* 196:901 (1987); Chothia et al., "Conformations of Immunoglobulin Hypervariable Regions," I 342:877 (1989); Martin and Thornton, "Structural Families in Loops of Homologous Proteins: Automatic Classification, Modelling and Application to Antibodies," *J. Mol. Biol.* 263:800 (1996), each of which is incorporated by reference in its entirety). Furthermore, there is a relationship between the adopted loop structure and the amino acid sequences surrounding it. The conformation of a particular canonical class is determined by the length of the loop and the amino acid residues residing at key positions within the loop, as well as within the conserved framework (i.e., outside of the loop). Assignment to a particular canonical class can therefore be made based on the presence of these key amino acid residues.

The term "polypeptide" is used interchangeably with the term "protein" and in its broadest sense refers to a compound of two or more subunit amino acids, amino acid analogs or peptidomimetics. The subunits may be linked by peptide bonds. In another embodiment, the subunit may be linked by other bonds, e.g., ester, ether, etc. As used herein the term "amino acid" refers to either natural and/or unnatural or synthetic amino acids, including glycine and both the D and L optical isomers, amino acid analogs and peptidomimetics. A peptide of three or more amino acids is commonly called an oligopeptide if the peptide chain is short. If the peptide chain is long, the peptide is commonly called a polypeptide or a protein.

"Specifically binds" or "binds specifically" or derivatives thereof when used in the context of antibodies, or antibody fragments, represents binding via domains encoded by immunoglobulin genes or fragments of immunoglobulin genes to one or more epitopes of a protein of interest, without preferentially binding other molecules in a sample containing a mixed population of molecules. Typically, an antibody binds to a cognate antigen with a $K_d$ of less than about $1 \times 10^{-8}$ M, as measured by a surface plasmon resonance assay, or a cell-binding assay. In a preferred embodiment, binding specificity is measure using biolayer interferometry. Phrases such as "[antigen]-specific" antibody are meant to convey that the recited antibody specifically binds the recited antigen.

"Polynucleotide," synonymously referred to as "nucleic acid molecule," "nucleotides" or "nucleic acids," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

A "vector" is a replicon, such as plasmid, phage, cosmid, or virus in which another nucleic acid segment may be operably inserted so as to bring about the replication or expression of the segment.

As used herein, the term "host cell" can be any type of cell, e.g., a primary cell, a cell in culture, or a cell from a cell line. In specific embodiments, the term "host cell" refers to a cell transfected with a nucleic acid molecule and the progeny or potential progeny of such a cell. Progeny of such a cell may not be identical to the parent cell transfected with the nucleic acid molecule, e.g., due to mutations or environmental influences that may occur in succeeding generations or integration of the nucleic acid molecule into the host cell genome. The terms "expression" and "production" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications. The expression or production of an antibody or antigen-binding fragment thereof may be within the cytoplasm of the cell, or into the extracellular milieu such as the growth medium of a cell culture. The meaning of "substantially the same" can differ depending on the context in which the term is used. Because of the natural sequence variation likely to exist among heavy and light chains and the genes encoding them, one would expect to find some level of variation within the amino acid sequences or the genes encoding the antibodies or antigen-binding fragments described herein, with little or no impact on their unique binding properties (e.g., specificity and affinity). Such an expectation is due in part to the degeneracy of the genetic code, as well as to the evolutionary success of conservative amino acid sequence variations, which do not appreciably alter the nature of the encoded protein. Accordingly, in the context of nucleic acid sequences, "substantially the same" means at least 65% identity between two or more sequences. Preferably, the term refers to at least 70% identity between two or more sequences, more preferably at least 75% identity, more preferably at least 80% identity, more preferably at least 85% identity, more preferably at least 90% identity, more preferably at least 91% identity, more preferably at least 92% identity, more preferably at least 93% identity, more preferably at least 94% identity, more preferably at least 95% identity, more preferably at least 96% identity, more preferably at least 97% identity, more preferably at least 98% identity, and more preferably at least 99% or greater identity. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The percent identity between two nucleotide or amino acid sequences may e.g. be determined using the algorithm of E. Meyers and W. Miller, Comput. Appl. Biosci 4, 11-17 (1988) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol. 48, 444-453 (1970) algorithm.

The degree of variation that may occur within the amino acid sequence of a protein without having a substantial effect on protein function is much lower than that of a nucleic acid sequence, since the same degeneracy principles do not apply to amino acid sequences. Accordingly, in the context of an antibody or antigen-binding fragment, "substantially the same" means antibodies or antigen-binding fragments having 90%, 91%, 92%, 93%, 94%, 95%, 96%, 97%, 98%, or 99% identity to the antibodies or antigen-binding fragments described. Other embodiments include proTGFβ1-GARP complex-selective antibodies, or antigen-binding fragments, that have framework, scaffold, or other non-binding regions that do not share significant identity with the proTGFβ1-GARP complex-selective antibodies and antigen-binding fragments described herein, but do incorporate one or more CDRs or other sequences needed to confer binding that are 90%, 91%, 92%, 93%, 94%, 95%, 96%, 97%, 98%, or 99% identical to such sequences described herein.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by techniques known to one of ordinary skill in the art, such as biolayer interferometry.

The term "subject" refers to human and non-human animals, including all vertebrates, e.g., mammals and non-mammals, such as non-human primates, mice, rabbits, sheep, dogs, cats, horses, cows, chickens, amphibians, and reptiles. In many embodiments of the described methods, the subject is a human.

proTGFβ1-GARP Complex-Selective Antibodies and Antigen-Binding Fragments

Described herein are isolated monoclonal antibodies or antigen-binding fragments that are proTGFβ1-GARP complex-selective antibodies. As used herein, the term "proTGFβ1-GARP complex-selective antibody" refers to an antibody with distinct affinity, specificity, and activity. proTGFβ1-GARP complex-selective antibodies may have: (1) a dissociation constant (Kd) of less than or equal to 1 nM for human proTGFβ1 when the proTGFβ1 is in a complex with human GARP in solution (e.g., as measured using a cell-free assay); (2) an inhibitory concentration (IC50) of less than or equal to 10 nM for inhibition of TGFβ1 growth factor release from cell-associated proTGFβ1-GARP complexes; (3) a greater than 100 fold selectivity (as measured by binding affinity, i.e., Kd value) for proTGFβ1-GARP complex over each of a TGFβ1 growth factor domain, a TGFβ2 growth factor domain, a TGFβ3 growth factor domain, proTGFβ1 covalently associated with LTBP1, proTGFβ1 covalently associated with LTBP3, and proTGFβ1 covalently associated with LRRC33; and (4) a lack of affinity for proTGFβ1 when not in a complex with GARP. In some cases, proTGFβ1-GARP complex-selective antibodies also have a greater than 100 fold selectivity for proTGFβ1-GARP complex over proTGFβ1 covalently associated with LTBP2 and/or LTBP4. The general structure of an antibody molecule comprises an antigen binding domain, which includes heavy and light chains, and the Fc domain, which serves a variety of functions, including complement fixation and binding antibody receptors.

The described proTGFβ1-GARP complex-selective antibodies or antigen-binding fragments include all isotypes, IgA, IgD, IgE, IgG and IgM, and synthetic multimers of the four-chain immunoglobulin structure. The described antibodies or antigen-binding fragments also include the IgY isotype generally found in hen or turkey serum and hen or turkey egg yolk.

The proTGFβ1-GARP complex-selective antibodies and antigen-binding fragments may be derived from any species by recombinant means. For example, the antibodies or antigen-binding fragments may be mouse, rat, goat, horse, swine, bovine, chicken, rabbit, camelid, donkey, human, or chimeric versions thereof. For use in administration to humans, non-human derived antibodies or antigen-binding fragments may be genetically or structurally altered to be less antigenic upon administration to a human patient.

In some embodiments, the antibodies or antigen-binding fragments are chimeric. As used herein, the term "chimeric" refers to an antibody, or antigen-binding fragment thereof, having at least some portion of at least one variable domain derived from the antibody amino acid sequence of a non-human mammal, a rodent, or a reptile, while the remaining portions of the antibody, or antigen-binding fragment thereof, are derived from a human.

In some embodiments, the antibodies are humanized antibodies. Humanized antibodies may be chimeric immunoglobulins, immunoglobulin chains or fragments thereof (such as Fv, Fab, Fab', F(ab')2 or other antigen-binding subsequences of antibodies) that contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin sequence. The humanized antibody may include at least a portion of an immunoglobulin constant region (Fc), typically that of a human immunoglobulin.

The antibodies or antigen-binding fragments described herein can occur in a variety of forms, but will include one or more of the antibody CDRs shown in Table 1.

In some embodiments, the proTGFβ1-GARP complex-selective antibodies or antigen-binding fragments are human IgG, or derivatives thereof. While the proTGFβ1-GARP complex-selective antibodies or antigen-binding fragments exemplified herein are human, the antibodies or antigen-binding fragments exemplified may be chimerized.

In some embodiments are provided proTGFβ1-GARP complex-selective antibodies comprising a heavy chain comprising a CDR1, a CDR2, and a CDR3 of any one of the antibodies described in Table 1 and a light chain comprising a CDR1, a CDR2, and a CDR3 of any one of the antibodies described in Table 1.

In some embodiments, the proTGFβ1-GARP complex-selective antibodies and antigen-binding fragments comprise a heavy chain CDR1 comprising SEQ ID NO: 4, a heavy chain CDR2 comprising SEQ ID NO: 5, a heavy chain CDR3 comprising SEQ ID NO: 6, a light chain CDR1 comprising SEQ ID NO: 7, a light chain CDR2 comprising SEQ ID NO: 8, and a light chain CDR3 comprising SEQ ID NO: 9. This proTGFβ1-GARP complex-selective antibody or antigen-binding fragment may comprise human framework sequences. This proTGFβ1-GARP complex-selective antibody or antigen-binding fragment may bind to the proTGFβ1 of the proTGFβ1-GARP complex with an affinity of 880 pM or less, may inhibit Treg function in vitro and may inhibit the activation of TGFβ1. In some embodiments, the proTGFβ1-GARP complex-selective antibodies and antigen-binding fragments comprise a heavy chain substantially the same as, or identical to, SEQ ID NO: 16 and a light chain substantially the same as, or identical to, SEQ ID NO: 17. The heavy chain and light chain of antibodies discussed in this paragraph are suitable for inclusion in bispecific constructs in which one arm is a proTGFβ1-GARP complex-selective antibody arm.

In some embodiments, the proTGFβ1-GARP complex-selective antibodies and antigen-binding fragments comprise a heavy chain CDR1 comprising SEQ ID NO: 10, a heavy chain CDR2 comprising SEQ ID NO: 11, a heavy chain CDR3 comprising SEQ ID NO: 12, a light chain CDR1 comprising SEQ ID NO: 13, a light chain CDR2 comprising SEQ ID NO: 14, and a light chain CDR3 comprising SEQ ID NO: 15. This proTGFβ1-GARP complex-selective antibody or antigen-binding fragment may comprise human framework sequences. This proTGFβ1-GARP complex-selective antibody or antigen-binding fragment may bind to proTGFβ1 of a proTGFβ1-GARP complex with an affinity of 880 pM or less, may inhibit Treg function in vitro and may and may inhibit the activation of TGFβ1. In some embodiments, the proTGFβ1-GARP complex-selective antibodies and antigen-binding fragments comprise a heavy chain substantially the same as, or identical to, SEQ ID NO: 18 and a light chain substantially the same as, or identical to, SEQ ID NO: 19. The heavy chain and light chain of antibodies discussed in this paragraph are suitable for inclusion in bispecific constructs in which one arm is a proTGFβ1-GARP complex-selective antibody arm.

The proTGFβ1-GARP complex-selective antibodies and antigen-binding fragments may have amino acid sequences having at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, and at least 99% or greater identity to the CDR amino acid sequences of SEQ ID NOS: 4-15 and variable region amino acid sequences of SEQ ID NOS: 16-19.

Also disclosed are isolated polynucleotides that encode the proTGFβ1-GARP complex-selective antibodies or antigen-binding fragments of the present disclosure. The isolated polynucleotides capable of encoding the variable domain segments provided herein may be included on the same, or different, vectors to produce antibodies or antigen-binding fragments.

Polynucleotides encoding recombinant antigen-binding proteins also are within the scope of the disclosure. In some embodiments, the polynucleotides described (and the peptides they encode) include a leader sequence. Any leader sequence known in the art may be employed. The leader sequence may include, but is not limited to, a restriction site or a translation start site.

The proTGFβ1-GARP complex-selective antibodies or antigen-binding fragments described herein include variants having single or multiple amino acid substitutions, deletions, or additions that retain the biological properties (e.g., binding affinity or immune effector activity) of the described proTGFβ1-GARP complex-selective antibodies or antigen-binding fragments. These variants may include: (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies or antigen-binding fragments described herein may include variants in which amino acid residues from one species are substituted for the corresponding residue in another species, either at the conserved or non-conserved positions. In other embodiments, amino acid residues at nonconserved positions are substituted with conservative or nonconservative residues. The techniques for obtaining these variants, including genetic (deletions, mutations, etc.), chemical, and enzymatic techniques, are known to persons having ordinary skill in the art.

The proTGFβ1-GARP complex-selective antibodies or antigen-binding fragments described herein may embody several antibody isotypes, such as IgM, IgD, IgG, IgA and IgE. In some embodiments the antibody isotype is IgG1, IgG2, IgG3, or IgG4 isotype, preferably IgG1 isotype. Antibody or antigen-binding fragment thereof specificity is largely determined by the amino acid sequence, and arrangement, of the CDRs. Therefore, the CDRs of one isotype may be transferred to another isotype without altering antigen specificity. Alternatively, techniques have been established to cause hybridomas to switch from producing one antibody isotype to another (isotype switching) without altering antigen specificity. Accordingly, such antibody isotypes are within the scope of the described antibodies or antigen-binding fragments.

The proTGFβ1-GARP complex-selective antibodies or antigen-binding fragments described herein have binding affinities for proTGFβ1 of a proTGFβ1-GARP complex that include a dissociation constant ($K_D$) of less than about 880 pM. The affinity of the described proTGFβ1-GARP complex-selective antibodies, or antigen-binding fragments, may be determined by a variety of methods known in the art, such as biolayer interferometry, surface plasmon resonance or ELISA-based methods. Assays for measuring affinity by biolayer interferometry include assays performed using an OctetRed 384 where the assay is performed at room temperature (e.g. at or near 25° C.), wherein the antibody capable of binding to proTGFβ1 of a proTGFβ1-GARP complex is captured on the streptavidin biosensors loaded with biotinylated proTGFβ1-GARP complex.

Also provided are vectors comprising the polynucleotides described herein. The vectors can be expression vectors. Recombinant expression vectors containing a sequence encoding a polypeptide of interest are thus contemplated as within the scope of this disclosure. The expression vector may contain one or more additional sequences such as but not limited to regulatory sequences (e.g., promoter, enhancer), a selection marker, and a polyadenylation signal. Vectors for transforming a wide variety of host cells are well known and include, but are not limited to, plasmids, phagemids, cosmids, baculoviruses, bacmids, bacterial artificial chromosomes (BACs), yeast artificial chromosomes (YACs), as well as other bacterial, yeast and viral vectors.

Recombinant expression vectors within the scope of the description include synthetic, genomic, or cDNA-derived nucleic acid fragments that encode at least one recombinant protein which may be operably linked to suitable regulatory elements. Such regulatory elements may include a transcriptional promoter, sequences encoding suitable mRNA ribosomal binding sites, and sequences that control the termination of transcription and translation. Expression vectors, especially mammalian expression vectors, may also include one or more nontranscribed elements such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a host may also be incorporated.

The transcriptional and translational control sequences in expression vectors to be used in transforming vertebrate cells may be provided by viral sources. Exemplary vectors may be constructed as described by Okayama and Berg, 3 *Mol. Cell. Biol.* 280 (1983).

In some embodiments, the antibody- or antigen-binding fragment-coding sequence is placed under control of a powerful constitutive promoter, such as the promoters for the following genes: hypoxanthine phosphoribosyl transferase (HPRT), adenosine deaminase, pyruvate kinase, beta-actin, human myosin, human hemoglobin, human muscle creatine, and others. In addition, many viral promoters function constitutively in eukaryotic cells and are suitable for use with the described embodiments. Such viral promoters include without limitation, Cytomegalovirus (CMV) immediate early promoter, the early and late promoters of SV40, the Mouse Mammary Tumor Virus (MMTV) promoter, the long terminal repeats (LTRs) of Maloney leukemia virus, Human Immunodeficiency Virus (HIV), Epstein Barr Virus (EBV), Rous Sarcoma Virus (RSV), and other retroviruses, and the thymidine kinase promoter of Herpes Simplex Virus. In one embodiment, the proTGFβ1-GARP complex-selective antibody or antigen-binding fragment thereof coding sequence is placed under control of an inducible promoter such as the metallothionein promoter, tetracycline-inducible promoter, doxycycline-inducible promoter, promoters that contain one or more interferon-stimulated response elements (ISRE) such as protein kinase R 2',5'-oligoadenylate synthetases, Mx genes, ADAR1, and the like.

Vectors described herein may contain one or more Internal Ribosome Entry Site(s) (IRES). Inclusion of an IRES sequence into fusion vectors may be beneficial for enhancing expression of some proteins. In some embodiments the vector system will include one or more polyadenylation sites (e.g., SV40), which may be upstream or downstream of any of the aforementioned nucleic acid sequences. Vector components may be contiguously linked, or arranged in a manner that provides optimal spacing for expressing the gene products (i.e., by the introduction of "spacer" nucleotides between the ORFs), or positioned in another way. Regulatory elements, such as the IRES motif, may also be arranged to provide optimal spacing for expression.

The vectors may comprise selection markers, which are well known in the art. Selection markers include positive and negative selection markers, for example, antibiotic resistance genes (e.g., neomycin resistance gene, a hygromycin resistance gene, a kanamycin resistance gene, a tetracycline resistance gene, a penicillin resistance gene), glutamate synthase genes, HSV-TK, HSV-TK derivatives for ganciclovir selection, or bacterial purine nucleoside phosphorylase gene for 6-methylpurine selection (Gadi et al., 7 *Gene Ther.* 1738-1743 (2000)). A nucleic acid sequence encoding a selection marker or the cloning site may be upstream or downstream of a nucleic acid sequence encoding a polypeptide of interest or cloning site.

The vectors described herein may be used to transform various cells with the genes encoding the described antibodies or antigen-binding fragments. For example, the vectors may be used to generate proTGFβ1-GARP complex-selective antibody or antigen-binding fragment-producing cells. Thus, another aspect features host cells transformed with vectors comprising a nucleic acid sequence encoding an antibody or antigen-binding fragment thereof that specifically binds proTGFβ1 of a proTGFβ1-GARP complex, such as the antibodies or antigen-binding fragments described and exemplified herein.

Numerous techniques are known in the art for the introduction of foreign genes into cells and may be used to construct the recombinant cells for purposes of carrying out the described methods, in accordance with the various embodiments described and exemplified herein. The technique used should provide for the stable transfer of the heterologous gene sequence to the host cell, such that the heterologous gene sequence is heritable and expressible by the cell progeny, and so that the necessary development and physiological functions of the recipient cells are not disrupted. Techniques which may be used include but are not limited to chromosome transfer (e.g., cell fusion, chromosome mediated gene transfer, micro cell mediated gene transfer), physical methods (e.g., transfection, spheroplast fusion, microinjection, electroporation, liposome carrier), viral vector transfer (e.g., recombinant DNA viruses, recombinant RNA viruses) and the like (described in Cline, 29 *Pharmac. Ther.* 69-92 (1985)). Calcium phosphate precipitation and polyethylene glycol (PEG)-induced fusion of bacterial protoplasts with mammalian cells may also be used to transform cells.

Cells suitable for use in the expression of the proTGFβ1-GARP complex-selective antibodies or antigen-binding fragments described herein are preferably eukaryotic cells, more preferably cells of plant, rodent, or human origin, for example but not limited to NSO, CHO, CHOK1, perC.6, Tk-ts13, BHK, HEK293 cells, COS-7, T98G, CV-1/EBNA, L cells, C127, 3T3, HeLa, NS1, Sp2/0 myeloma cells, and BHK cell lines, among others. In addition, expression of antibodies may be accomplished using hybridoma cells. Methods for producing hybridomas are well established in the art.

Cells transformed with expression vectors described herein may be selected or screened for recombinant expression of the antibodies or antigen-binding fragments described herein. Recombinant-positive cells are expanded and screened for subclones exhibiting a desired phenotype, such as high level expression, enhanced growth properties, or the ability to yield proteins with desired biochemical characteristics, for example, due to protein modification or altered post-translational modifications. These phenotypes may be due to inherent properties of a given subclone or to mutation. Mutations may be effected through the use of chemicals, UV-wavelength light, radiation, viruses, insertional mutagens, inhibition of DNA mismatch repair, or a combination of such methods.

Methods of Using proTGFβ1-GARP Complex-Selective Antibodies for Treatment

Provided herein are proTGFβ1-GARP complex-selective antibodies or antigen-binding fragments thereof for use in therapy. In particular, these antibodies or antigen-binding fragments may be useful in treating cancer. As described above, active TGFβ1 released from Tregs inhibit the actions of other T cells. Thus, inhibiting the TGFβ1-mediated immunosuppressive function represents an attractive approach for boosting an immune response against a variety of cancers. The proTGFβ1-GARP complex-selective antibodies can be used to treat both solid tumors, as well as hematological cancers, including leukemia.

The antibodies for use in these methods include those described herein above, for example a proTGFβ1-GARP complex-selective antibody or antigen-binding fragment with the features set out in Table 1, for example the CDRs or variable domain sequences, and in the further discussion of these antibodies.

In some embodiments described herein, immune effector properties of the proTGFβ1-GARP complex-selective antibodies may be modulated through Fc modifications by techniques known to those skilled in the art. For example, Fc effector functions such as C1q binding, complement dependent cytotoxicity (CDC), antibody-dependent cell-mediated cytotoxicity (ADCC), antibody-dependent cell-mediated phagocytosis (ADCP), down regulation of cell surface receptors (e.g., B cell receptor; BCR), etc. may be provided and/or controlled by modifying residues in the Fc responsible for these activities.

"Antibody-dependent cell-mediated cytotoxicity" or "ADCC" refers to a cell-mediated reaction in which non-specific cytotoxic cells that express Fc receptors (FcRs) (e.g. Natural Killer (NK) cells, neutrophils, and macrophages) recognize bound antibody on a target cell and subsequently cause lysis of the target cell.

The ability of monoclonal antibodies to induce ADCC can be enhanced by engineering their oligosaccharide component. Human IgG1 or IgG3 are N-glycosylated at Asn297 with the majority of the glycans in the well-known biantennary G0, G0F, G1, G1F, G2 or G2F forms. Antibodies produced by non-engineered CHO cells typically have a glycan fucose content of about at least 85%. The removal of the core fucose from the biantennary complex-type oligosaccharides attached to the Fc regions enhances the ADCC of antibodies via improved Fc.gamma.RIIIa binding without altering antigen binding or CDC activity. Such mAbs can be achieved using different methods reported to lead to the successful expression of relatively high defucosylated antibodies bearing the biantennary complex-type of Fc oligosaccharides such as control of culture osmolality (Konno et al., Cytotechnology 64:249-65, 2012), application of a variant CHO line Lec13 as the host cell line (Shields et al., J Biol Chem 277:26733-26740, 2002), application of a variant CHO line EB66 as the host cell line (Olivier et al., MAbs; 2(4), 2010; Epub ahead of print; PMID:20562582), application of a rat hybridoma cell line YB2/0 as the host cell line (Shinkawa et al., J Biol Chem 278:3466-3473, 2003), introduction of small interfering RNA specifically against the .alpha. 1,6-fucosyltrasferase (FUT8) gene (Mori et al., Biotechnol Bioeng 88:901-908, 2004), or coexpression of beta-1,4-N-acetylglucosaminyltransferase III and Golgi alpha-mannosidase II or a potent alpha-mannosidase I inhibitor, kifunensine (Ferrara et al., J Biol Chem 281:5032-5036, 2006, Ferrara et al., Biotechnol Bioeng 93:851-861, 2006; Xhou et al., Biotechnol Bioeng 99:652-65, 2008).

In some embodiments described herein, ADCC elicited by the proTGFβ1-GARP complex-selective antibodies may also be enhanced by certain substitutions in the antibody Fc. Exemplary substitutions are for example substitutions at amino acid positions 256, 290, 298, 312, 356, 330, 333, 334, 360, 378 or 430 (residue numbering according to the EU index) as described in U.S. Pat. No. 6,737,056.

Pharmaceutical Compositions and Administration

The pharmaceutical compositions provided herein comprise: a) an effective amount of a proTGFβ1-GARP complex-selective antibody or antibody fragment of the present invention, and b) a pharmaceutically acceptable carrier, which may be inert or physiologically active. In preferred embodiments, the proTGFβ1-GARP complex-selective antibody is a proTGFβ1-GARP complex-selective antibody as described herein, or an antigen-binding fragment thereof. As used herein, the term "pharmaceutically acceptable carriers" includes any and all solvents, dispersion media, coatings, antibacterial and antifungal agents, and the like that are physiologically compatible. Examples of suitable carriers, diluents and/or excipients include one or more of water, saline, phosphate buffered saline, dextrose, glycerol, ethanol, and the like, as well as any combination thereof. In many cases, it will be preferable to include isotonic agents, such as sugars, polyalcohols, or sodium chloride in the composition. In particular, relevant examples of suitable carrier include: (1) Dulbecco's phosphate buffered saline, pH.about.7.4, containing or not containing about 1 mg/mL to 25 mg/mL human serum albumin, (2) 0.9% saline (0.9% w/v sodium chloride (NaCl)), and (3) 5% (w/v) dextrose; and may also contain an antioxidant such as tryptamine and a stabilizing agent such as Tween 20®.

The compositions herein may also contain a further therapeutic agent, as necessary for the particular disorder being treated. Preferably, the proTGFβ1-GARP complex-selective antibodies or antibody fragment and the supplementary active compound will have complementary activities that do not adversely affect each other. In a preferred embodiment, the further therapeutic agent is cytarabine, an anthracycline, histamine dihydrochloride, or interleukin 2. In a preferred embodiment, the further therapeutic agent is a chemotherapeutic agent.

The compositions of the invention may be in a variety of forms. These include for example liquid, semi-solid, and solid dosage forms, but the preferred form depends on the intended mode of administration and therapeutic application. Typical preferred compositions are in the form of injectable or infusible solutions. The preferred mode of administration is parenteral (e.g. intravenous, intramuscular, intraperitoneal, subcutaneous). In a preferred embodiment, the compositions of the invention are administered intravenously as a bolus or by continuous infusion over a period of time. In another preferred embodiment, they are injected by intramuscular, subcutaneous, intra-articular, intrasynovial, intratumoral, peritumoral, intralesional, or perilesional routes, to exert local as well as systemic therapeutic effects.

Sterile compositions for parenteral administration can be prepared by incorporating the antibody, antibody fragment or antibody conjugate of the present invention in the required amount in the appropriate solvent, followed by sterilization by microfiltration. As solvent or vehicle, there may be used water, saline, phosphate buffered saline, dextrose, glycerol, ethanol, and the like, as well as combination thereof. In many cases, it will be preferable to include isotonic agents, such as sugars, polyalcohols, or sodium chloride in the composition. These compositions may also contain adjuvants, in particular wetting, isotonizing, emulsifying, dispersing and stabilizing agents. Sterile compositions for parenteral administration may also be prepared in the form of sterile solid compositions which may be dissolved at the time of use in sterile water or any other injectable sterile medium.

The proTGFβ1-GARP complex-selective antibodies or antibody fragment may also be orally administered. As solid compositions for oral administration, tablets, pills, powders (gelatine capsules, sachets) or granules may be used. In these compositions, the active ingredient according to the invention is mixed with one or more inert diluents, such as starch, cellulose, sucrose, lactose or silica, under an argon stream. These compositions may also comprise substances other than diluents, for example one or more lubricants such as magnesium stearate or talc, a coloring, a coating (sugar-coated tablet) or a glaze.

As liquid compositions for oral administration, there may be used pharmaceutically acceptable solutions, suspensions, emulsions, syrups and elixirs containing inert diluents such as water, ethanol, glycerol, vegetable oils or paraffin oil. These compositions may comprise substances other than diluents, for example wetting, sweetening, thickening, flavoring or stabilizing products.

The doses depend on the desired effect, the duration of the treatment and the route of administration used; they are generally between 5 mg and 1000 mg per day orally for an adult with unit doses ranging from 1 mg to 250 mg of active substance. In general, the doctor will determine the appropriate dosage depending on the age, weight and any other factors specific to the subject to be treated.

In a preferred embodiment, proTGFβ1-GARP complex-selective antibodies or antibody fragments of the invention are used for the treatment of a hyperproliferative disorder in a mammal. In a more preferred embodiment, one of the pharmaceutical compositions disclosed above, and which contains a proTGFβ1-GARP complex-selective antibody or antibody fragment of the invention, is used for the treatment of a hyperproliferative disorder in a mammal. In one embodiment, the disorder is a cancer. A variety of different cancerous tumors such as for an adrenocortical carcinoma, anal cancer, bladder cancer, brain tumor, glioma, breast carcinoma, carcinoid tumor, cervical cancer, colon carcinoma, endometrial cancer, esophageal cancer, extrahepatic bile duct cancer, Ewings tumor, extracranial germ cell tumor, eye cancer, gall bladder cancer, gastric cancer, germ cell tumor, gestational trophoblastic tumor, head and neck cancer, hypopharyngeal cancer, islet cell carcinoma, kidney cancer, laryngeal cancer, leukemia, lip and oral cavity cancer, liver cancer, lung cancer, lymphoma, melanoma, mesothelioma, merkel cell carcinoma, metastatic squamous head and neck cancer, myeloma, neoplasm, nasopharyngeal cancer, neuroblastoma, oral cancer, oropharyngeal cancer, osteosarcoma, ovarian cancer, pancreatic cancer, sinus and nasal cancer, parathyroid cancer, penile cancer, pheochromocytoma cancer, pituitary cancer, plasma cell neoplasm, prostate cancer, rhabdomyosarcoma, rectal cancer, renal cell carcinoma, salivary gland cancer, skin cancer, Kaposi's sarcoma, T-cell lymphoma, soft tissue sarcoma, stomach cancer, testicular cancer, thymoma, thyroid cancer, urethral cancer, uterine cancer, vaginal cancer, vulvar cancer, or Wilms' tumor can be treated with the antibodies described herein.

In treating any of the foregoing cancers, the treatment methods that are provided can be utilized to inhibit further tumor growth, induce tumor regression, increase progression-free survival and/or extend overall survival in an individual that has a tumor. In some embodiments, the proTGFβ1-GARP complex-selective antibodies can also delay or prevent the onset of metastasis. Progress in treatment can be monitored using various methods. For instance, inhibition can result in reduced tumor size and/or a decrease in metabolic activity within the tumor. Both of these parameters can be measured by MRI or PET scans for example. Inhibition can also be monitored by biopsy to ascertain the level of necrosis, tumor cell death and the level of vascularity within the tumor. The extent of metastasis can be monitored using known methods. Accordingly, the pharmaceutical compositions of the invention are useful in the treatment or prevention of metastasis of a variety of cancers, including (but not limited to) the following: melanoma, lung, head and neck, renal cell, colorectal, breast, prostate, endometrial, bladder, kidney, esophageal, testicular, ovarian, squamous cell carcinoma (e.g., squamous cell carcinoma of the head and neck—SCCHN), uveal melanoma, follicular lymphoma, cervical, brain, pancreatic, liver, lymphoma, Hodgkin's disease, multiple myeloma, gastric, and astrocyctic.

Similarly, further provided herein is a method for inhibiting the growth of selected cell populations comprising contacting TGFβ1-expressing immune cells with an effective amount of a proTGFβ1-GARP complex-selective antibody or antibody fragment of the present disclosure, either alone or in combination with other therapeutic agents. In preferred embodiments, the proTGFβ1-GARP complex-selective antibody is a proTGFβ1-GARP complex-selective antibody as described herein, or an antigen-binding fragment thereof. In a preferred embodiment, the further therapeutic agent is an immunotherapy i.e., an immunostimulatory agent that induces or enhances an immune response. Such agents can include, for example: 1) activators of dendritic cells, 2) vaccine adjuvants, 3) T cell stimulators, 4) inhibitors of immune checkpoints, and 5) inhibitors of suppressive cells, cytokines and/or enzymes. Thus, in one embodiment, an antibody is administered with a vaccine.

For clinical use, a therapeutically effective amount of the proTGFβ1-GARP complex-selective antibody or antigen-binding fragment is administered to a subject in need thereof. For example, the proTGFβ1-GARP complex-selective antibodies and antigen-binding fragments thereof may be useful in the treatment of cancerous tumors that contain TGFβ1-positive immune cells. In preferred embodiments the proTGFβ1-GARP complex-selective antibody is a proTGFβ1-GARP complex-selective antibody as described herein, or an antigen-binding fragment thereof. In some embodiments, the subject is a mammal, preferably a human.

In some embodiments, the proTGFβ1-GARP complex-selective antibody or antigen-binding fragment will be administered as a solution that has been tested for sterility.

Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage.

The efficient dosages and the dosage regimens for the proTGFβ1-GARP complex-selective antibodies and fragments depend on the disease or condition to be treated and may be determined by one skilled in the art. An exemplary, non-limiting range for a therapeutically effective amount of a compound of the present invention is about 0.001-10 mg/kg, such as about 0.001-5 mg/kg, for example about 0.001-2 mg/kg, such as about 0.001-1 mg/kg, for instance about 0.001, about 0.01, about 0.1, about 1 or about 10 mg/kg.

A physician or veterinarian having ordinary skill in the art may readily determine and prescribe the effective amount of the pharmaceutical composition required. For example, the physician or veterinarian could start doses of the proTGFβ1-GARP complex-selective antibody or fragment employed in the pharmaceutical composition at levels lower than that required in order to achieve the desired therapeutic effect and gradually increase the dosage until the desired effect is achieved. In general, a suitable daily dose of a proTGFβ1-GARP complex-selective antibody of the present invention will be that amount of the compound which is the lowest dose effective to produce a therapeutic effect. Administration may e.g. be parenteral, such as intravenous, intramuscular or subcutaneous. In one embodiment, the proTGFβ1-GARP complex-selective antibody or fragment may be administered by infusion in a weekly dosage of calculated by mg/m$^2$. Such dosages can, for example, be based on the mg/kg dosages provided above according to the following: dose (mg/kg)×70. Such administration may be repeated, e.g., 1 to 8 times, such as 3 to 5 times. The administration may be performed by continuous infusion over a period of from 2 to 24 hr, such as of from 2 to 12 hr. In one embodiment, the proTGFβ1-GARP complex-selective antibody or fragment may be administered by slow continuous infusion over a long period, such as more than 24 hours, in order to reduce toxic side effects.

In one embodiment, the proTGFβ1-GARP complex-selective antibody or fragment may be administered in a weekly dosage calculated as a fixed dose for up to eight times, such as from four to six times when given once a week. Such regimen may be repeated one or more times as necessary, for example, after six months or twelve months. Such fixed dosages can, for example, be based on the mg/kg dosages provided above, with a body weight estimate of 70 kg. The dosage may be determined or adjusted by measuring the amount of proTGFβ1-GARP complex-selective antibody of the present invention in the blood upon administration by for instance taking out a biological sample and using anti-idiotypic antibodies which target the antigen binding region of the proTGFβ1-GARP complex-selective antibodies of the present invention.

In one embodiment, the proTGFβ1-GARP complex-selective antibody or fragment may be administered by maintenance therapy, such as, e.g., once a week for a period of six months or more.

A proTGFβ1-GARP complex-selective antibody or fragment may also be administered prophylactically in order to reduce the risk of developing cancer, delay the onset of the occurrence of an event in cancer progression, and/or reduce the risk of recurrence when a cancer is in remission.

The proTGFβ1-GARP complex-selective antibodies and fragments thereof as described herein may also be administered in combination therapy, i.e., combined with other therapeutic agents relevant for the disease or condition to be treated. Accordingly, in one embodiment, the antibody-containing medicament is for combination with one or more further therapeutic agent, such as a chemotherapeutic agent. In some embodiments, the other therapeutic agents include, but are not limited to, anti-neoplastic agents including alkylating agents including: nitrogen mustards, such as mechlorethamine, cyclophosphamide, ifosfamide, melphalan and chlorambucil; nitrosoureas, such as carmustine (BCNU), lomustine (CCNU), and semustine (methyl-CCNU); Temodal™ (temozolamide), ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil (5FU), fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; pipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinum coordination complexes such as cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p-DDD) and aminoglutethimide; hormones and antagonists including adrenocorticosteroid antagonists such as prednisone and equivalents, dexamethasone and aminoglutethimide; Gemzar™ (gemcitabine), progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide. Therapies targeting epigenetic mechanism including, but not limited to, histone deacetylase inhibitors, demethylating agents (e.g., Vidaza) and release of transcriptional repression (ATRA) therapies can also be combined with the proTGFβ1-GARP complex-selective antibodies.

Additional specific examples of chemotherapeutic agents include, taxol, taxenes (e.g., docetaxel and Taxotere), modified paclitaxel (e.g., Abraxane and Opaxio) doxorubicin, Avastin®, Sutent, Nexavar, and other multikinase inhibitors, cisplatin and carboplatin, etoposide, gemcitabine, and vinblastine. Specific inhibitors of other kinases can also be used in combination with the proTGFβ1-GARP complex-selective antibodies, including but not limited to, MAPK pathway inhibitors (e.g., inhibitors of ERK, JNK and p38), PI3kinase/AKT inhibitors and Pim inhibitors. Other inhibitors include Hsp90 inhibitors, proteasome inhibitors (e.g., Velcade) and multiple mechanism of action inhibitors such as Trisenox.

Such combined administration may be simultaneous, separate or sequential, in any order. For simultaneous administration the agents may be administered as one composition or as separate compositions, as appropriate.

In one embodiment, a proTGFβ1-GARP complex-selective antibody or fragment thereof is combined with an agent that stimulates antigen-presenting cells. Examples of such agents include various CD40 agonists, such as an agonist anti-CD40 antibody or CD40L.

Some methods involve administering a proTGFβ1-GARP complex-selective antibody or fragment thereof with a vaccine adjuvant. Such adjuvants include, for instance, IL-12, and various Toll Like Receptor (TLR) agonists, including CpG (a TLR 9 agonist), monophosphoryl lipid A (MPL—a TLR4 agonist), PolyI:C or PolyICLC (TLR3 agonist), and resiquimod and 852A (TLR 7/8 agonists).

In other therapeutic approaches, a proTGFβ1-GARP complex-selective antibody is administered in combination with T cell growth factors such as IL-15 and/or IL-17, or activators of these molecules. In related methods, a T cell stimulator is combined with a proTGFβ1-GARP complex-selective antibody. Such stimulators include agonists of 4-1BB, such as agonist anti-4-1BB antibodies and 4-1BBL.

In one embodiment, a proTGFβ1-GARP complex-selective antibody or fragment thereof is administered with a T cell checkpoint inhibitor, e.g., molecules that send an inhibitory signal to the immune system. Examples of such agents include inhibitors of PD-1 or PD-L1 (B7-H1), such as anti-PD-1 antibodies, including nivolumab (Bristol-Myers Squibb) and pembrolizumab, also known as MK-3475 (Merck), pidilizumab (Curetech), AMP-224 (Amplimmune), and anti-PD-L1 antibodies, including MPDL3280A (Roche), MDX-1105 (Bristol Myer Squibb), MEDI-4736 (AstraZeneca) and MSB-0010718C (Merck). Other checkpoint inhibitors include antagonists of CTLA-4, such as anti-CTLA-4 antibodies. An exemplary anti-CTLA4 antibody is Yervoy® (ipilimumab) marketed by Bristol-Myers Squibb. Other exemplary CTLA-4 antibodies include tremelimumab (Pfizer), Ticilimumab (AstraZeneca) and AMGP-224 (Glaxo Smith Kline).

In yet other methods, a proTGFβ1-GARP complex-selective antibody or fragment thereof is administered in combination with an inhibitor of an enzyme that has an immunosuppressive effect. An example is 1-methyl tryptophan (1MT), which is a small molecule inhibitor of indoleamine 2,3-dioxygenase.

The proTGFβ1-GARP complex-selective antibody or fragment thereof can also be used in combination with T-VEC (talimogene laherparepvec) by Amgen.

In certain embodiments, the proTGFβ1-GARP complex-selective antibody or fragment thereof is administered in combination with a bispecific antibody. The bispecific antibody can direct the immune system of a host, in particular the cyotoxic activity of T-cells, against cancer cells.

A proTGFβ1-GARP complex-selective antibody or fragment thereof can also be administered in combination with a variety of targeted therapies. Examples of targeted therapies include, but are not limited to, use of therapeutic antibodies. Exemplary antibodies include, but are not limited to, those which bind to cell surface proteins Her2, CDC20, CDC33, mucin-like glycoprotein, and epidermal growth factor receptor (EGFR) present on tumor cells, OX40, PD-1, CTLA-4, and optionally induce a cytostatic and/or cytotoxic effect on tumor cells displaying these proteins. Exemplary antibodies also include HERCEPTIN® (trastuzumab), which may be used to treat breast cancer and other forms of cancer, and RITUXAN® (rituximab), ZEVALIN™ (ibritumomab tiuxetan), and LYMPHOCIDE™ (epratuzumab), which may be used to treat non-Hodgkin's lymphoma and other forms of cancer. Certain exemplary antibodies also include panitumumab (VECTIBIX®), ERBITUX® (IMC-C225); BEXXAR™ (iodine 131 tositumomab); KDR (kinase domain receptor) inhibitors; anti VEGF antibodies and antagonists (e.g., Avastin® and VEGAF-TRAP); anti VEGF receptor antibodies and antigen binding regions; anti-Ang-1 and Ang-2 antibodies and antigen binding regions; antibodies to Tie-2 and other Ang-1 and Ang-2 receptors; Tie-2 ligands; antibodies against Tie-2 kinase inhibitors; inhibitors of Hif-1a, and Campath™ (Alemtuzumab). In certain embodiments, cancer therapy agents are polypeptides which selectively induce apoptosis in tumor cells, including, but not limited to, the TNF-related polypeptide TRAIL.

In one embodiment, a proTGFβ1-GARP complex-selective antibody or fragment thereof, as provided herein is used in combination with one or more anti-angiogenic agents that decrease angiogenesis. Certain such agents include, but are not limited to, IL-8 antagonists; Campath, B-FGF; FGF antagonists; Tek antagonists (Cerretti et al., U.S. Publication No. 2003/0162712; Cerretti et al., U.S. Pat. No. 6,413,932, and Cerretti et al., U.S. Pat. No. 6,521,424); anti-TWEAK agents (which include, but are not limited to, antibodies and antigen binding regions); soluble TWEAK receptor antagonists (Wiley, U.S. Pat. No. 6,727,225); an ADAM distintegrin domain to antagonize the binding of integrin to its ligands (Fanslow et al., U.S. Publication No. 2002/0042368); anti-eph receptor and anti-ephrin antibodies; antigen binding regions, or antagonists (U.S. Pat. Nos. 5,981,245; 5,728,813; 5,969,110; 6,596,852; 6,232,447; 6,057,124); anti-VEGF agents (e.g., antibodies or antigen binding regions that specifically bind VEGF, or soluble VEGF receptors or a ligand binding regions thereof) such as Avastin® or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as panitumumab, IRESSA™ (gefitinib), TARCEVA™ (erlotinib), anti-Ang-1 and anti-Ang-2 agents (e.g., antibodies or antigen binding regions specifically binding thereto or to their receptors, e.g., Tie-2/TEK), and anti-Tie-2 kinase inhibitory agents (e.g., antibodies or antigen binding regions that specifically bind and inhibit the activity of growth factors, such as antagonists of hepatocyte growth factor (HGF, also known as Scatter Factor), and antibodies or antigen binding regions that specifically bind its receptor "c-met" (e.g., rilotumumab and AMG 337, Amgen); anti-PDGF-BB antagonists; antibodies and antigen binding regions to PDGF-BB ligands; and PDGFR kinase inhibitors.

Other anti-angiogenic agents that can be used in combination with a proTGFβ1-GARP complex-selective antibody or fragment thereof include agents such as MMP-2 (matrix-metalloproteinase 2) inhibitors, MMP-9 (matrix-metalloproteinase 9) inhibitors, and COX-II (cyclooxygenase II) inhibitors. Examples of useful COX-II inhibitors include CELEBREX™ (celecoxib), valdecoxib, and rofecoxib.

A proTGFβ1-GARP complex-selective antibody or fragment thereof as provided herein can also be used in combination with a growth factor inhibitor. Examples of such agents, include, but are not limited to, agents that can inhibit EGF-R (epidermal growth factor receptor) responses, such as EGF-R antibodies (e.g., panitumumab (VECTIBIX®)), EGF antibodies, and molecules that are EGF-R inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN® (Genentech, Inc.). EGF-R inhibitors are described in, for example in U.S. Pat. No. 5,747,498, WO 98/14451, WO 95/19970, and WO 98/02434.

In some treatment applications, particularly when the cancer has metastasized to the bone such that the bone is negatively impacted, it can be useful to administer a proTGFβ1-GARP complex-selective antibody or fragment thereof with a therapeutic agent that inhibits further bone loss or aids in restoring bone that has been lost. Accordingly, the proTGFβ1-GARP complex-selective antibody or fragment thereof can be administered with a therapeutically effective amount of a bone growth promoting (anabolic) agent or a bone anti-resorptive agent including but not limited to: bone morphogenic factors designated BMP-1 to BMP-12; transforming growth factor-β and TGF-β family members; fibroblast growth factors FGF-1 to FGF-10; interleukin-1 inhibitors (including IL-1ra, antibodies to IL-1 and antibodies to IL-1 receptors); TNFα inhibitors (including etanercept, adalibumab and infliximab); RANK ligand inhibitors (including soluble RANK, osteoprotegerin and antagonistic antibodies that specifically bind RANK or RANK ligand, such as denosumab (XGEVA®)), Dkk-1 inhibitors (e.g., anti-Dkk-1 antibodies), parathyroid hormone, E series prostaglandins, bisphosphonates and bone-enhancing minerals such as fluoride and calcium. Anabolic agents that can be used in combination with the proTGFβ1-GARP complex-selective antibodies and functional fragments thereof include parathyroid hormone and insulin-like growth factor (IGF), wherein the latter agent is preferably complexed with an IGF binding protein. An IL-1 receptor antagonist suitable for such combination treatment is described in WO89/11540 and a suitable soluble TNF receptor-1 is described in WO98/01555. Exemplary RANK ligand antagonists are disclosed, for example, in WO 03/086289, WO 03/002713, U.S. Pat. Nos. 6,740,511 and 6,479,635.

In one embodiment, a method for treating a cancer includes administration of a therapeutically effective amount of a proTGFβ1-GARP complex-selective antibody as described herein, along with radiotherapy to a subject in need thereof. Radiotherapy may comprise radiation or associated administration of radiopharmaceuticals to a patient. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

Methods of Detecting proTGFβ1-GARP Complex

Provided herein are methods for detecting proTGFβ1-GARP complex in a biological sample by contacting the sample with an antibody, or antigen-binding fragment thereof, described herein. As described herein, the sample may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like. In some embodiments the described methods include detecting proTGFβ1-GARP complex in a biological sample by contacting the sample with any of the proTGFβ1-GARP complex-selective antibodies or antigen-binding fragments thereof described herein.

In some embodiments the sample may be contacted with more than one of the proTGFβ1-GARP complex-selective antibodies or antigen-binding fragments described herein. For example, a sample may be contacted with a first proTGFβ1-GARP complex-selective antibody, or antigen-binding fragment thereof, and then contacted with a second proTGFβ1-GARP complex-selective antibody, or antigen-binding fragment thereof, wherein the first antibody or antigen-binding fragment and the second antibody or antigen-binding fragment are not the same antibody or antigen-binding fragment. In some embodiments, the first antibody, or antigen-binding fragment thereof, may be affixed to a surface, such as a multiwell plate, chip, or similar substrate prior to contacting the sample. In other embodiments the first antibody, or antigen-binding fragment thereof, may not be affixed, or attached, to anything at all prior to contacting the sample.

The described proTGFβ1-GARP complex-selective antibodies and antigen-binding fragments may be detectably labeled. In some embodiments labeled antibodies and antigen-binding fragments may facilitate the detection of proTGFβ1-GARP complex via the methods described herein. Many such labels are readily known to those skilled in the art. For example, suitable labels include, but should not be considered limited to, radiolabels, fluorescent labels, epitope tags, biotin, chromophore labels, ECL labels, or enzymes. More specifically, the described labels include ruthenium, $^{111}$In-DOTA, diethylenetriaminepentaacetic acid (DTPA), horseradish peroxidase, alkaline phosphatase and beta-galactosidase, poly-histidine (HIS tag), acridine dyes, cyanine dyes, fluorone dyes, oxazin dyes, phenanthridine dyes, rhodamine dyes, Alexafluor® dyes, and the like.

The described proTGFβ1-GARP complex-selective antibodies and antigen-binding fragments may be used in a variety of assays to detect proTGFβ1-GARP complex in a biological sample. Some suitable assays include, but should not be considered limited to, western blot analysis, radioimmunoassay, surface plasmon resonance, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

Kits for Detecting proTGFβ1-GARP Complex

Provided herein are kits for detecting proTGFβ1-GARP complex in a biological sample. These kits include one or more of the proTGFβ1-GARP complex-selective antibodies described herein, or an antigen-binding fragment thereof, and instructions for use of the kit.

The provided proTGFβ1-GARP complex-selective antibody, or antigen-binding fragment, may be in solution; lyophilized; affixed to a substrate, carrier, or plate; or detectably labeled.

The described kits may also include additional components useful for performing the methods described herein. By way of example, the kits may comprise means for obtaining a sample from a subject, a control or reference sample, e.g., a sample from a subject having slowly progressing cancer and/or a subject not having cancer, one or more sample compartments, and/or instructional material which describes performance of a method of the invention and tissue specific controls or standards.

The means for determining the level of proTGFβ1-GARP complex can further include, for example, buffers or other reagents for use in an assay for determining the level of proTGFβ1-GARP complex. The instructions can be, for example, printed instructions for performing the assay and/or instructions for evaluating the level of expression of proTGFβ1-GARP complex.

The described kits may also include means for isolating a sample from a subject. These means can comprise one or more items of equipment or reagents that can be used to obtain a fluid or tissue from a subject. The means for obtaining a sample from a subject may also comprise means for isolating blood components, such as serum, from a blood sample. Preferably, the kit is designed for use with a human subject.

EXAMPLES

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the invention.

Example 1: Discovery of proTGFβ1-GARP Complex-Selective Antibodies Using Phage Display Technology Antibody development campaigns were undertaken to develop proTGFβ1-GARP complex-selective antibodies. The ChemPartner proprietary fully human naïve phage display library (Chempartner, Shanghai, China) was used as a source of human antibody fragments. The library was first negatively panned against a combined mixture of biotinylated sGARP (SEQ ID NO:1) and LTBP1-proTGFβ1 (SEQ ID NOs 2 and 3) to remove scFv fragments that bind the undesired LTBP1-proTGFb1 complex or the uncomplexed sGARP protein. The output of the deselected library was then panned against sGARP-proTGFβ1 for several rounds. Twenty-five scFvs that bound specifically to sGARP-proTGFβ1 were selected based on unique HCDR3 sequences, desired complex selectivity, and sequence liabilities. The unique heavy chain V-regions were cloned into human IgG4 expression vectors, the unique light chains were cloned into human kappa expression vectors, and the resultant proTGFβ1-GARP complex-selective antibody candidates were tested again for binding activity in an ELISA. The top binders from this assay were selected for further characterization.

Example 2: Inhibition of Human Treg Function by 4B1C1 and 4B16B9 In Vitro

The proTGFβ1-GARP complex-selective antibody candidates produced in the previous example were tested for inhibition of human Treg function in an in vitro suppression assay. Activated CD4$^+$CD25Hi suppressor cells were used as a source of Tregs and CFSE-labeled CD4+CD25− effector T cells (Teff cells) were used as targets for suppression of proliferation. Cells were incubated at a 1 Treg/1 Teff ratio with plate-bound anti-CD3, soluble anti-CD28 and in the presence or absence of proTGFβ1-GARP complex-selective antibody candidates. The Tregs inhibited the proliferation of Teff cells by ~50% as compared to T effectors only. Proliferation levels of Teff (incubated with Tregs) were restored in the presence of 4B1C1, and partially restored by 4B16B9, when compared to the Treg/Teff control or hIgG4 groups (FIG. 1). These results confirm the activity of TGF-β1 in the immunosuppression by human Tregs and indicate that 4B1C1 and 4B16B9 can partially block this activity in vitro, similar to the positive control neutralizing TGFβ antibody 1D11 (R&D Systems catalog number MAB-1835).

TABLE 2

CDR sequences of the two proTGFβ1-GARP complex-selective antibody candidates that showed binding against proTGFβ1-GARP complex and inhibition of human Treg function in vitro

| ID | HC-CDR1 | HC-CDR2 | HC-CDR3 | LC-CDR1 | LC-CDR2 | LC-CDR3 |
|---|---|---|---|---|---|---|
| 4B1C1 | DYTMH (4) | LISWDGGSTYYADSVKG (5) | DADDSTFDI (6) | RASQSVSRNLA (7) | WASTRES (8) | QQYYSVPYT (9) |
| 4B16B9 | SYAIS (10) | GIIPMFGTTNYAQKFQG (11) | DREWEPAYGMDV (12) | IGTSSDVGGYNYVS (13) | DVSNRPS (14) | SAYTVSSTWV (15) |

(SEQ ID NO:)

VH and VL of the two proTGFβ1-GARP complex-selective antibody candidates are shown below in Table 3.

TABLE 3

Heavy chain and light chain sequences of the two proTGFβ1-GARP complex-selective antibody candidates that showed binding against proTGFβ1-GARP complex and inhibition of human Treg function in vitro.

| mAb ID | Heavy Chain Amino Acid Sequence | SEQ ID NO: | Light Chain Amino Acid Sequence | SEQ ID NO: |
|---|---|---|---|---|
| 4B1C1 | EVQLVQSGGVVVQPG GSLRLSCAASGFTFDD YTMHWVRQAPGKGLE | 16 | ETTLTQSPATLSVSPGE RVTLSCRASQSVSRNL AWYQQKPGQPPKLLIY | 17 |

TABLE 3-continued

Heavy chain and light chain sequences of the two proTGFβ1-GARP complex-selective antibody candidates that showed binding against proTGFβ1-GARP complex and inhibition of human Treg function in vitro.

| mAb ID | Heavy Chain Amino Acid Sequence | SEQ ID NO: | Light Chain Amino Acid Sequence | SEQ ID NO: |
|---|---|---|---|---|
| | WVSLISWDGGSTYYA DSVKGRFTISRDNSKN SLYLQMNSLRTEDTAL YYCAKDADDSTFDIW GQGTMVTVSSASTKGP SVFPLAPCSRSTSESTA ALGCLVKDYFPEPVTV SWNSGALTSGVHTFPA VLQSSGLYSLSSVVTV PSSSLGTKTYTCNVDH KPSNTKVDKRVESKY GPPCPPCPAPEFLGGPS VFLFPPKPKDTLMISRT PEVTCVVVDVSQEDPE VQFNWYVDGVEVHN AKTKPREEQFNSTYRV VSVLTVLHQDWLNGK EYKCKVSNKGLPSSIE KTISKAKGQPREPQVY TLPPSQEEMTKNQVSL TCLVKGFYPSDIAVEW ESNGQPENNYKTTPPV LDSDGSFFLYSRLTVD KSRWQEGNVFSCSVM HEALHNHYTQKSLSLS LG | | WASTRESGVPDRFSGS GSGTDFTLTISSLQAED VAVYYCQQYYSVPYT FGQGTKLEIKRTVAAP SVFIFPPSDEQLKSGTA SVVCLLNNFYPREAKV QWKVDNALQSGNSQE SVTEQDSKDSTYSLSST LTLSKADYEKHKVYA CEVTHQGLSSPVTKSF NRGEC | |
| 4B16B9 | QMQLVQSGAEVKKPG SSVKVSCKASGGTFSS YAISWVRQAPGQGLE WMGGIIPMFGTTNYA QKFQGRVTIIADESTST AYMELRSLRSDDTAV YYCARDREWEPAYGM DVWGQGTTVTVSSASAS TKGPSVFPLAPCSRSTS ESTAALGCLVKDYFPE PVTVSWNSGALTSGV HTFPAVLQSSGLYSLSS VVTVPSSSLGTKTYTC NVDHKPSNTKVDKRV ESKYGPPCPPCPAPEFL GGPSVFLFPPKPKDTL MISRTPEVTCVVVDVS QEDPEVQFNWYVDGV EVHNAKTKPREEQFNS TYRVVSVLTVLHQDW LNGKEYKCKVSNKGL PSSIEKTISKAKGQPRE PQVYTLPPSQEEMTKN QVSLTCLVKGFYPSDI AVEWESNGQPENNYK TTPPVLDSDGSFFLYSR LTVDKSRWQEGNVFS CSVMHEALHNHYTQK SLSLSLG | 18 | QSALTQPASVSGSPGQ SITISCIGTSSDVGGYN YVSWYQQHPGKAPKL MIYDVSNRPSGVSNRF SGSKSGNTASLTISGLQ AEDEAMYYCSAYTVS STWVFGGGTKVTVLGG QPKAAPSVTLFPPSSEE LQANKATLVCLISDFY PGAVTVAWKADSSPV KAGVETTTPSKQSNNK YAASSYLSLTPEQWKS HRSYSCQVTHEGSTVE KTVAPTECS | 19 |

Variable regions are underlined.

Example 3: TGFβ1 Bioassay

The ability of the proTGFβ1-GARP complex-selective antibody candidates to regulate the levels of active TGFβ1 was measured using TMLC reporter cells with an integrated TGFβ/Smad3-responsive luciferase expression unit. Briefly, HEK293 or Sw480 cells were transiently transfected with either human proTGFβ1 and LTBP1 or human proTGFβ1 and GARP expression plasmids. The cells were allowed to recover from the transfection and to express proTGFβ1 in complex with either LTBP1 or GARP for 24 hours at 37° C., at which point the assay could be performed. To set up the assay, the transient transfectants were co-cultured with SW480β6 cells, which stably express the TGFβ1-activating integrin αVββ6. To confirm that the assay worked as intended, media samples with known concentrations of TGF-β1 growth factor were added to TMLC reporter cell cultures to generate a standard curve.

ProTGFβ1-GARP complex-selective antibody candidates (10 μg/mL) were combined with transfected cells and added to TMLC reporter cell cultures. The plates were then incubated at 37° C. for 16 hours. Successful TGFβ1 signaling was expected to activate the SMAD2/3 pathway, followed by luciferase expression, which could be detected by adding Bright-Glo, as indicated by the manufacturer (Promega), and measuring the resultant luminescence in a Biotek Synergy H1 plate reader (Biotek).

4B1C1 and 4B16B9 antibodies induced significantly decreased luciferase expression compared to treatment with the control group, indicating that these antibodies regulate the levels of active TGFβ1 growth factor and reduce TGFβ1-mediated signaling in the cells. This effect is similar to the impact of the positive control neutralizing TGFβ antibody 1D11.

Example 4: Affinity Measurements by Biolayer Interferometry

The binding affinities of the proTGFβ1-GARP complex-selective antibody candidates to proTGFβ1-GARP complexes were measured by biolayer interferometry on an OctetRed 384 (Fortebio, Menlo Park, Calif.). Strepavidin biosensors (Fortebio, Cat. No. 18-5020) were loaded with biotinylated sGARP-proTGFβ1 complex at 20 µg/ml in sodium acetate buffer, pH 5, washed in the same buffer and transferred to wells containing 10 µg/mL proTGFβ1-GARP complex-selective antibody candidates in the same buffer. The dissociation constant was obtained by non-linear fitting of the responses to a steady state algorithm using Octet software (Table 4). Similar affinities were obtained by kinetic fitting.

TABLE 4

Octet affinity results for proTGFβ1-GARP complex-selective antibody candidates binding to human proTGFβ1-GARP complex.

| mAb | proTGFβ1-GARP complex | $K_D$ (nM) |
|---|---|---|
| 4B1C1 | human | 0.114 +/− 0.004 |
| 4B16B9 | human | 0.880 +/− 0.036 |

To ascertain binding specificity, 4B1C1 and 4B16B9 were screened as above for binding to TGFβ1, TGFβ2, TGFβ3, proTGFβ1-LTBP1, proTGFβ1-LTBP3 and proTGFβ1-LRRC33. As described above, antibodies were tested at 10 µg/ml and antigens at 20 µg/ml and tested under the following conditions. These studies demonstrated no discernible binding of antibodies to any antigen other than the proTGFβ1-GARP complex and shown in FIG. 4.

TABLE 5

Assay conditions for determination of antibody binding specificity

| Assay Step Number | Step Type | Assay Time in Seconds |
|---|---|---|
| 1 | Baseline | 60 |
| 2 | Antigen Loading | 180 |
| 3 | Baseline | 60 |
| 4 | Association | 300 |
| 5 | Dissociation | 600 |

Example 5: Dose Response Assay

The concentration dependence of proTGFβ1-GARP complex-selective antibody candidate regulation of levels of active TGFβ1 was measured using TMLC reporter cells with an integrated TGFβ/Smad3-responsive luciferase expression unit as described in EXAMPLE 3 with the only difference being that proTGFβ1-GARP complex-selective antibody candidates were added to experimental wells at various concentrations.

Figure 3:
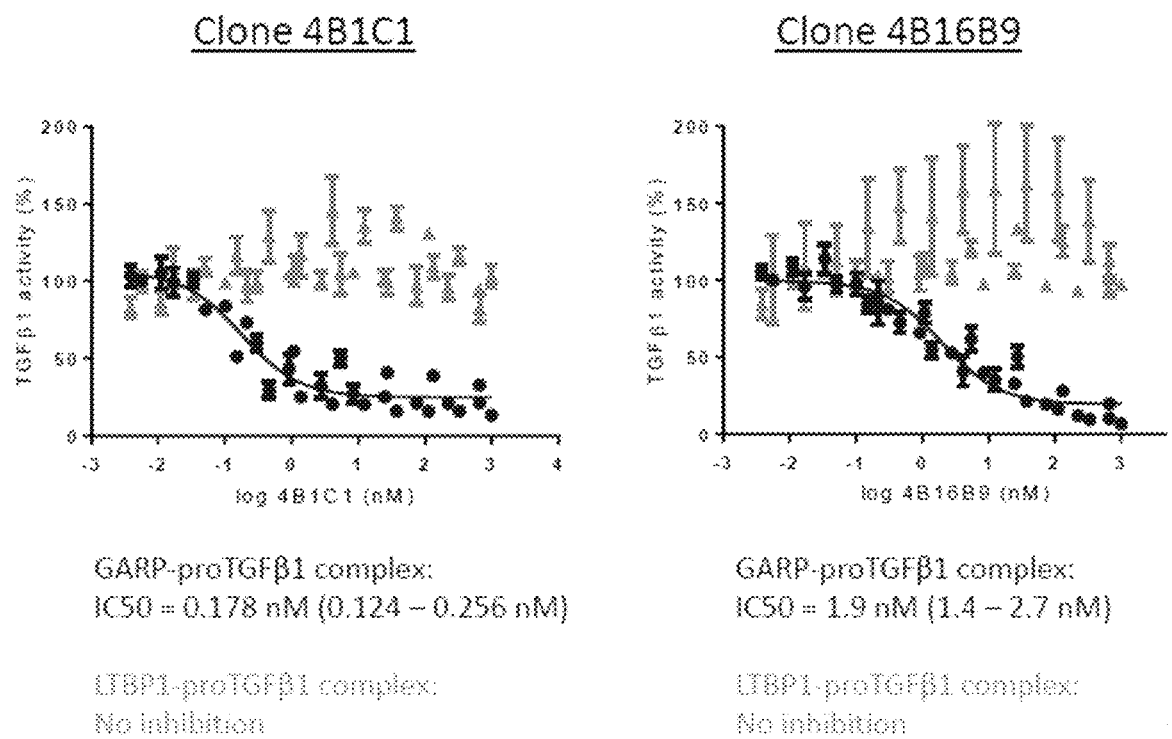
FIG. 3 shows the dose-dependent inhibition of TGFβ1 activity by 4B1C1 and 4B16B9.

4B1C1 and 4B16B9 demonstrated they could inhibit TGFβ1 activation in a dose-dependent manner with IC50s of 0.178 nM and 1.9 nM, respectively (FIG. 3).

Example 6: Antibody Characterization proTGFβ1-GARP complex-selective antibody candidates were measured by biolayer interferometry on an OctetRed 384 (Fortebio, Menlo Park, Calif.) for selectivity for proTGFβ1-GARP complex over other protein complexes (FIG. 4). 4B1C1 and 4B16B9 exhibited a dissociation constant (Kd) of less than 1 nM for proTGFβ1-GARP complex, while exhibiting no detectable binding to proTGFβ1-LTBP1 or proTGFβ1-LTBP3 complexes. 4B1C1 and 4B16B9 also did not exhibit binding to TGFβ1, TGFβ2, or TGFβ3 growth factors.

Antibody binding to proTGFβ1-LRRC33 complexes was also tested. proTGFβ1-LRRC33 complex was expressed and purified by size-exclusion chromatography (SEC) and the formation of non-aggregated complexes was confirmed by analytical SEC. Binding of 4B1C1 and 4B16B9 to purified proTGFβ1-LRRC33 complex was then tested by OctetRed 384 (Fortebio, Menlo Park, Calif.) analysis as described in Example 4. For that, 4B1C1 or 4B16B9 was captured on anti-human Fc tips, and binding of either proTGFβ1-GARP or proTGFβ1-LRRC33 was detected by Octet. In contrast to proTGFβ1-GARP, no binding of 4B1C1 or 4B16B9 to proTGFβ1-LRRC33 complex was detected.

| | | Bried Description of the Sequence Listing | | |
|---|---|---|---|---|
| SEQ ID NO: | Type | Species | Description | Sequence |
| 1 | PRT | human | sGARP | HQDKVPCKMVDKKVSCQVLGLLQV PSVLPPDTETLDLSGNQLRSILASPLG FYTALRHLDLSTNEISFLQ PGAFQALTHLEHLSLAHNRLAMATA LSAGGLGPLPRVTSLDLSGNSLYSGL LERLLGEAPSLHTLSLAEN SLTRLTRHTFRDMPALEQLDLHSNVL MDIEDGAFEGLPRLTHLNLSRNSLTCI SDFSLQQLRVLDLSCNS IEAFQTASQPQAEFQLTWLDLRENKL LHFPDLAALPRLIYLNLSNNLIRLPTG PPQDSKGIHAPSEGWSA LPLSAPSGNASGRPLSQLLNLDLSYN EIELIPDSFLEHLTSLCFLNLSRNCLRT FEARRLGSLPCLMLLD |

-continued

Bried Description of the Sequence Listing

| SEQ ID NO: | Type | Species | Description | Sequence |
|---|---|---|---|---|
| | | | | LSHNALETLELGARALGSLRTLLLQG NALRDLPPYTFANLASLQRLNLQGN RVSPCGGPDEPGPSGCVAF SGITSLRSLSLVDNEIELLRAGAFLHT PLTELDLSSNPGLEVATGALGGLEAS LEVLALQGNGLMVLQVD LPCFICLKRLNLAENRLSHLPAWTQA VSLEVLDLRNNSFSLLPGSAMGGLET SLRRLYLQGNPLSCCGNG WLAAQLHQGRVDVDATQDLICRFSS QEEVSLSHVRPEDCEKGGLKNINHH HHHH |
| 2 | PRT | human | proTGFβ1 | LSTCKTIDMELVKRKRIEAIRGQILSK LRLASPPSQGEVPPGPLPEAVLALYN STRDRVAGESAEPEPEP EADYYAKEVTRVLMVETHNEIYDKF KQSTHSIYMFFNTSELREAVPEPVLLS RAELRLLRLKLKVEQHVE LYQKYSNNSWRYLSNRLLAPSDSPE WLSFDVTGVVRQWLSRGGEIEGFRL SAHCSCDSRDNTLQVDINGF TTGRRGDLATIHGMNRPFLLLMATPL ERAQHLQSSRHRRALDTNYCFSSTEK NCCVRQLYIDFRKDLGWK WIHEPKGYHANFCLGPCPYIWSLDTQ YSKVLALYNQHNPGASAAPCCVPQA LEPLPIVYYVGRKPKVEQL SNMIVRSCKCS |
| 3 | PRT | human | LTBP1 fragment | EINECTVNPDICGAGHCINLPVRYTCI CYEGYRFSEQQRKCVDIDECTQVQH LCSQGRCENTEGSFLCIC PAGFMASEEGTNCIDVDECLRPDVC GEGHCVNTVGAFRCEYCDSGYRMT QRGRCEDIDECLNPSTCPDEQ CVNSPGSYQCVPCTEGFRGWNGQCL DVDECLEPNVCANGDCSNLEGSYMC SCHKGYTRTPDHKHCRDIDE CQQGNLCVNGQCKNTEGSFRCTCGQ GYQLSAAKDQCEDIDECQHRHLCAH GQCRNTEGSFQCVCDQGYRA SGLGDHCEDINECLEDKSVCQRGDCI NTAGSYDCTCPDGFQLDDNKTCQDI NECEHPGLCGPQGECLNTE GSFHCVCQQGFSISADGRTCEDIDEC VNNTVCDSHGFCDNTAGSFRCLCYQ GFQAPQDGQGCVDVNECEL LSGVCGEAFCENVEGSFLCVCADEN QEYSPMTGQCRSRTSTDLDVDVDQP KEEKKECYYNLNDASLCDNV LAPNVTKQECCCTSGVGWGDNCEIF PCPVLGTAEFTEMCPKGKGFVPAGES SSEAGGENYKDADECLLFG QEICKNGFCLNTRPGYECYCKQGTY YDPVKLQCFDMDECQDPSSCIDGQC VNTEGSYNCFCTHPMVLDAS EKRCIHHHH |
| 4 | PRT | human | 4B1C1-HCDR1 | DYTMH |
| 5 | PRT | human | 4B1C1-HCDR2 | LISWDGGSTYYADSVKG |
| 6 | PRT | human | 4B1C1-HCDR3 | DADDSTFDI |
| 7 | PRT | human | 4B1C1-LCDR1 | RASQSVSRNLA |
| 8 | PRT | human | 4B1C1-LCDR2 | WASTRES |

| SEQ ID NO: | Type | Species | Description | Sequence |
|---|---|---|---|---|
| 9 | PRT | human | 4B1C1-LCDR3 | QQYYSVPYT |
| 10 | PRT | human | 4B16B9-HCDR1 | SYAIS |
| 11 | PRT | human | 4B16B9-HCDR2 | GIIPMFGTTNYAQKFQG |
| 12 | PRT | human | 4B16B9-HCDR3 | DREWEPAYGMDV |
| 13 | PRT | human | 4B16B9-LCDR1 | IGTSSDVGGYNYVS |
| 14 | PRT | human | 4B16B9-LCDR2 | DVSNRPS |
| 15 | PRT | human | 4B16B9-LCDR3 | SAYTVSSTWV |
| 16 | PRT | human | 4B1C1-Heavy Chain | EVQLVQSGGVVVQPGGSLRLSCAAS GFTFDDYTMHWVRQAPGKGLEWVS LISWDGGSTYYADSVKGRFTISRDNS KNSLYLQMNSLRTEDTALYYCAKDA DDSTFDIWGQGTMVTVSSASTKGPS VFPLAPCSRSTSESTAALGCLVKDYF PEPVTVSWNSGALTSGVHTFPAVLQS SGLYSLSSVVTVPSSSLGTKTYTCNV DHKPSNTKVDKRVESKYGPPCPPCPA PEFLGGPSVFLFPPKPKDTLMISRTPE VTCVVVDVSQEDPEVQFNWYVDGV EVHNAKTKPREEQFNSTYRVVSVLT VLHQDWLNGKEYKCKVSNKGLPSSI EKTISKAKGQPREPQVYTLPPSQEEM TKNQVSLTCLVKGFYPSDIAVEWESN GQPENNYKTTPPVLDSDGSFFLYSRL TVDKSRWQEGNVFSCSVMHEALHN HYTQKSLSLSLG |
| 17 | PRT | human | 4B1C1-Light Chain | ETTLTQSPATLSVSPGERVTLSCRASQ SVSRNLAWYQQKPGQPPKLLIYVVAS TRESGVPDRFSGSGSGTDFTLTISSLQ AEDVAVYYCQQYYSVPYTFGQGTKL EIKRTVAAPSVFIFPPSDEQLKSGTAS VVCLLNNFYPREAKVQWKVDNALQ SGNSQESVTEQDSKDSTYSLSSTLTLS KADYEKHKVYACEVTHQGLSSPVTK SFNRGEC |
| 18 | PRT | human | 4B16B9-Heavy Chain | QMQLVQSGAEVKKPGSSVKVSCKAS GGTFSSYAISWVRQAPGQGLEWMGG IIPMFGTTNYAQKFQGRVTIIADESTS TAYMELRSLRSDDTAVYYCARDRE WEPAYGMDVWGQGTTVTVSSASTK GPSVFPLAPCSRSTSESTAALGCLVK DYFPEPVTVSWNSGALTSGVHTFPA VLQSSGLYSLSSVVTVPSSSLGTKTY TCNVDHKPSNTKVDKRVESKYGPPC PPCPAPEFLGGPSVFLFPPKPKDTLMI SRTPEVTCVVVDVSQEDPEVQFNWY VDGVEVHNAKTKPREEQFNSTYRVV SVLTVLHQDWLNGKEYKCKVSNKG LPSSIEKTISKAKGQPREPQVYTLPPS QEEMTKNQVSLTCLVKGFYPSDIAVE WESNGQPENNYKTTPPVLDSDGSFFL YSRLTVDKSRWQEGNVFSCSVMHEA LHNHYTQKSLSLSLG |
| 19 | PRT | human | 4b16B9-Light Chain | QSALTQPASVSGSPGQSITISCIGTSSD VGGYNYVSWYQQHPGKAPKLMIYD VSNRPSGVSNRFSGSKSGNTASLTISG LQAEDEAMYYCSAYTVSSTWVFGG GTKVTVLGQPKAAPSVTLFPPSSEEL |

Bried Description of the Sequence Listing

| SEQ ID NO: | Type | Species | Description | Sequence |
|---|---|---|---|---|
| | | | | QANKATLVCLISDFYPGAVTVAWKA DSSPVKAGVETTTPSKQSNNKYAASS YLSLTPEQWKSHRSYSCQVTHEGST VEKTVAPTECS |

We claim:

1. An antibody or antigen-binding fragment thereof, wherein the antibody or antigen-binding fragment thereof specifically binds to human proTGFβ1 in a complex with human glycoprotein A repetitions predominant (proTGFβ1-GARP complex), wherein the antibody or antigen-binding fragment thereof comprises:
   a. a heavy chain complementarity determining region (CDR) 1 comprising the amino acid sequence of SEQ ID NO: 4, a heavy chain CDR2 comprising the amino acid sequence of SEQ ID NO: 5, and a heavy chain CDR3 comprising the amino acid sequence of SEQ ID NO: 6, and a light chain CDR1 comprising the amino acid sequence of SEQ ID NO: 7, a light chain CDR2 comprising the amino acid sequence of SEQ ID NO: 8, and a light chain CDR3 comprising the amino acid sequence of SEQ ID NO: 9; or
   b. a heavy chain CDR1 comprising the amino acid sequence of SEQ ID NO: 10, a heavy chain CDR2 comprising the amino acid sequence of SEQ ID NO: 11, and a heavy chain CDR3 comprising the amino acid sequence of SEQ ID NO: 12, and a light chain CDR1 comprising the amino acid sequence of SEQ ID NO: 13, a light chain CDR2 comprising the amino acid sequence of SEQ ID NO: 14, and a light chain CDR3 comprising the amino acid sequence of SEQ ID NO: 15.

2. The antibody or antigen-binding fragment thereof of claim 1, wherein the antibody or antigen-binding fragment thereof inhibits regulatory T cell (Treg) function in vitro.

3. The antibody or antigen-binding fragment thereof of claim 1, wherein the antibody or antigen-binding fragment thereof inhibits the activation of TGFβ1.

4. The antibody or antigen-binding fragment thereof of claim 1, wherein the antibody or antigen-binding fragment thereof binds to an epitope of human proTGFβ1 modified as a result of complex formation with human GARP.

5. The antibody or antigen-binding fragment thereof of claim 1, wherein the antibody or antigen-binding fragment thereof binds to a polypeptide comprising the amino acid sequence of SEQ ID NO: 2 in the presence of a polypeptide comprising the amino acid sequence of SEQ ID NO: 1.

6. The antibody or antigen-binding fragment thereof of claim 5, wherein the antibody or antigen-binding fragment thereof specifically binds to human proTGFβ1 with a binding affinity of at least 880 pM as measured by biolayer interferometry assay.

7. The antibody or antigen-binding fragment thereof of claim 5, wherein the antibody or antigen-binding fragment thereof binds to human proTGFβ1 with a dissociation constant (Kd) of less than or equal to 1 nM for human proTGFβ1 in a complex with human glycoprotein A repetitions predominant (proTGFβ1-GARP complex) and wherein said proTGFβ1-GARP complex is in solution.

8. The antigen-binding fragment thereof of claim 1, wherein the antigen-binding fragment is a Fab fragment, a Fab2 fragment, or a single chain antibody.

9. The antibody or antigen-binding fragment thereof of claim 1, wherein the antibody or antigen-binding fragment is recombinant.

10. The antibody or antigen-binding fragment thereof of claim 1, wherein the antibody or antigen-binding fragment thereof are of lgG1, lgG2, lgG3, or lgG4 isotype.

11. The antibody or antigen-binding fragment thereof of claim 10, wherein the antibody is an lgG4 isotype.

12. A polynucleotide encoding the antibody or antigen-binding fragment thereof of claim 1.

13. A vector comprising the polynucleotide of claim 12.

14. A host cell comprising the vector of claim 13.

15. A process for the production of an antibody or antigen-binding fragment thereof, comprising:
culturing the host cell of claim 14 under the conditions allowing the expression of the antibody or antigen-binding fragment thereof, and
recovering the antibody or antigen-binding fragment thereof from the culture.

16. A pharmaceutical composition comprising the antibody or antigen-binding fragment thereof of claim 1 and a pharmaceutically acceptable carrier.

17. A kit comprising the antibody or antigen-binding fragment thereof of claim 1 and packaging for the same.

18. The antibody or antigen-binding fragment thereof of claim 1, wherein the antibody or antigen-binding fragment specifically binds to human proTGFβ1 in a complex with human glycoprotein A repetitions predominant (proTGFβ1-GARP complex);
wherein said complex is in solution;
wherein the antibody or antigen-binding fragment thereof has no detectable binding according to a biolayer interferometry assay to any of the following:
a TGFβ1 growth factor domain,
a TGFβ2 growth factor domain,
a TGFβ3 growth factor domain,
a proTGFβ1 covalently associated with LTBP1,
a proTGFβ1 covalently associated with LTBP3,
a proTGFβ1 covalently associated with LRRC33, or
a proTGFβ1 that is not associated with human GARP; and
wherein the antibody or antigen-binding fragment thereof has an inhibitory concentration (IC50) of less than or equal to 10 nM for inhibition of TGFB1 growth factor release from a cell-associated proTGFβ1-GARP complex.

19. A method of treating a subject with an infectious disease or hyperproliferative disorder comprising administering to a subject in need thereof the antibody or antigen-binding fragment thereof of claim 1.

20. The method of claim 19, wherein the antibody or antigen-binding fragment thereof is administered in combination with one or more additional therapies or therapeutic agents selected from:
(a) a chemotherapeutic agent,
(b) radiotherapy, and
(c) a T-cell checkpoint inhibitor selected from an anti-PD-1 antibody, an anti-PD-L1 antibody, or an anti-CTLA-4 antibody.

21. The method of claim 19, wherein the hyperproliferative disorder is cancer.

22. The method of claim 21, wherein the cancer is kidney cancer or renal cell carcinoma.

23. The method of claim 21, wherein the treatment results in one or more of the following:
inhibition of further tumor growth,
induction of tumor regression,
increase of progression-free survival,
extension of overall survival, or
delay or prevention of the onset of metastasis.

24. An antibody or antigen-binding fragment thereof, comprising:
a. a heavy chain comprising an amino acid sequence that is at least 90% identical to the amino acid sequence of SEQ ID NO: 16 and a light chain comprising an amino acid sequence that is at least 90% identical to the amino acid sequence of SEQ ID NO: 17,
wherein the antibody or antigen-binding fragment thereof comprises heavy chain CDRs 1-3 comprising the amino acid sequences of SEQ ID NOs: 4-6, respectively, and light chain CDRs 1-3 comprising the amino acid sequences of SEQ ID NOs: 7-9, respectively; or
b. a heavy chain comprising an amino acid sequence that is at least 90% identical to the amino acid sequence of SEQ ID NO: 18 and a light chain comprising an amino acid sequence that is at least 90% identical to the amino acid sequence of SEQ ID NO: 19,
wherein the antibody or antigen-binding fragment thereof comprises heavy chain CDRs 1-3 comprising the amino acid sequences of SEQ ID NOs: 10-12, respectively, and light chain CDRs 1-3 comprising the amino acid sequences of SEQ ID NOs: 13-15, respectively.

25. The antibody or antigen-binding fragment thereof of claim 24, wherein
a. the heavy chain comprises the amino acid sequence of SEQ ID NO: 16 and the light chain comprises the amino acid sequence of SEQ ID NO: 17; or
b. the heavy chain comprises the amino acid sequence of SEQ ID NO: 18 and the light chain comprises the amino acid sequence of SEQ ID NO: 19.

26. An antibody or antigen-binding fragment thereof, comprising:
a. a heavy chain variable region comprising an amino acid sequence that is at least 90% identical to amino acids 1-118 of SEQ ID NO: 16 and a light chain variable region comprising an amino acid sequence that is at least 90% identity to amino acids 1-107 of SEQ ID NO: 17,
wherein the antibody or antigen-binding fragment thereof comprises heavy chain CDRs 1-3 comprising the amino acid sequences of SEQ ID NOs: 4, 5, and 6, respectively, and light chain CDRs 1-3 comprising the amino acid sequences of SEQ ID NOs: 7, 8, and 9, respectively;

b. a heavy chain variable region comprising an amino acid sequence that is at least 90% identical to amino acids 1-121 of SEQ ID NO: 18 and a light chain variable region comprising an amino acid sequence that is at least 90% identical to amino acids 1-110 of SEQ ID NO: 19,
wherein the antibody or antigen-binding fragment thereof comprises heavy chain CDRs 1-3 comprising the amino acid sequences of SEQ ID NOs: 10-12, respectively, and light chain CDRs 1-3 comprising the amino acid sequences of SEQ ID NOs: 13-15, respectively;
c. a heavy chain variable region comprising amino acids 1-118 of SEQ ID NO: 16 and a light chain variable region sequence comprising amino acids 1-107 of SEQ ID NO: 17; or
d. a heavy chain variable region comprising amino acids 1-121 of SEQ ID NO: 18 and a light chain variable region sequence comprising amino acids 1-110 of SEQ ID NO: 19.

* * * * *

SEQUENCE LISTING

<160> NUMBER OF SEQ ID NOS: 19

<210> SEQ ID NO 1
<211> LENGTH: 614
<212> TYPE: PRT
<213> ORGANISM: Homo sapiens

<400> SEQUENCE: 1

```
His Gln Asp Lys Val Pro Cys Lys Met Val Asp Lys Val Ser Cys
1               5                   10                  15

Gln Val Leu Gly Leu Leu Gln Val Pro Ser Val Leu Pro Pro Asp Thr
            20                  25                  30

Glu Thr Leu Asp Leu Ser Gly Asn Gln Leu Arg Ser Ile Leu Ala Ser
        35                  40                  45

Pro Leu Gly Phe Tyr Thr Ala Leu Arg His Leu Asp Leu Ser Thr Asn
    50                  55                  60

Glu Ile Ser Phe Leu Gln Pro Gly Ala Phe Gln Ala Leu Thr His Leu
65                  70                  75                  80

Glu His Leu Ser Leu Ala His Asn Arg Leu Ala Met Ala Thr Ala Leu
                85                  90                  95

Ser Ala Gly Gly Leu Gly Pro Leu Pro Arg Val Thr Ser Leu Asp Leu
            100                 105                 110

Ser Gly Asn Ser Leu Tyr Ser Gly Leu Leu Glu Arg Leu Leu Gly Glu
        115                 120                 125

Ala Pro Ser Leu His Thr Leu Ser Leu Ala Glu Asn Ser Leu Thr Arg
    130                 135                 140

Leu Thr Arg His Thr Phe Arg Asp Met Pro Ala Leu Glu Gln Leu Asp
145                 150                 155                 160

Leu His Ser Asn Val Leu Met Asp Ile Glu Asp Gly Ala Phe Glu Gly
                165                 170                 175

Leu Pro Arg Leu Thr His Leu Asn Leu Ser Arg Asn Ser Leu Thr Cys
            180                 185                 190

Ile Ser Asp Phe Ser Leu Gln Gln Leu Arg Val Leu Asp Leu Ser Cys
        195                 200                 205

Asn Ser Ile Glu Ala Phe Gln Thr Ala Ser Gln Pro Gln Ala Glu Phe
    210                 215                 220

Gln Leu Thr Trp Leu Asp Leu Arg Glu Asn Lys Leu Leu His Phe Pro
225                 230                 235                 240

Asp Leu Ala Ala Leu Pro Arg Leu Ile Tyr Leu Asn Leu Ser Asn Asn
                245                 250                 255

Leu Ile Arg Leu Pro Thr Gly Pro Pro Gln Asp Ser Lys Gly Ile His
            260                 265                 270

Ala Pro Ser Glu Gly Trp Ser Ala Leu Pro Leu Ser Ala Pro Ser Gly
        275                 280                 285
```

```
Asn Ala Ser Gly Arg Pro Leu Ser Gln Leu Leu Asn Leu Asp Leu Ser
    290                 295                 300

Tyr Asn Glu Ile Glu Leu Ile Pro Asp Ser Phe Leu Glu His Leu Thr
305                 310                 315                 320

Ser Leu Cys Phe Leu Asn Leu Ser Arg Asn Cys Leu Arg Thr Phe Glu
                325                 330                 335

Ala Arg Arg Leu Gly Ser Leu Pro Cys Leu Met Leu Leu Asp Leu Ser
            340                 345                 350

His Asn Ala Leu Glu Thr Leu Glu Leu Gly Ala Arg Ala Leu Gly Ser
        355                 360                 365

Leu Arg Thr Leu Leu Leu Gln Gly Asn Ala Leu Arg Asp Leu Pro Pro
    370                 375                 380

Tyr Thr Phe Ala Asn Leu Ala Ser Leu Gln Arg Leu Asn Leu Gln Gly
385                 390                 395                 400

Asn Arg Val Ser Pro Cys Gly Gly Pro Asp Glu Pro Gly Pro Ser Gly
                405                 410                 415

Cys Val Ala Phe Ser Gly Ile Thr Ser Leu Arg Ser Leu Ser Leu Val
            420                 425                 430

Asp Asn Glu Ile Glu Leu Leu Arg Ala Gly Ala Phe Leu His Thr Pro
        435                 440                 445

Leu Thr Glu Leu Asp Leu Ser Ser Asn Pro Gly Leu Glu Val Ala Thr
    450                 455                 460

Gly Ala Leu Gly Gly Leu Glu Ala Ser Leu Glu Val Leu Ala Leu Gln
465                 470                 475                 480

Gly Asn Gly Leu Met Val Leu Gln Val Asp Leu Pro Cys Phe Ile Cys
                485                 490                 495

Leu Lys Arg Leu Asn Leu Ala Glu Asn Arg Leu Ser His Leu Pro Ala
            500                 505                 510

Trp Thr Gln Ala Val Ser Leu Glu Val Leu Asp Leu Arg Asn Asn Ser
        515                 520                 525

Phe Ser Leu Leu Pro Gly Ser Ala Met Gly Gly Leu Glu Thr Ser Leu
    530                 535                 540

Arg Arg Leu Tyr Leu Gln Gly Asn Pro Leu Ser Cys Cys Gly Asn Gly
545                 550                 555                 560

Trp Leu Ala Ala Gln Leu His Gln Gly Arg Val Asp Val Asp Ala Thr
                565                 570                 575

Gln Asp Leu Ile Cys Arg Phe Ser Ser Gln Glu Val Ser Leu Ser
            580                 585                 590

His Val Arg Pro Glu Asp Cys Glu Lys Gly Gly Leu Lys Asn Ile Asn
        595                 600                 605

His His His His His His
    610

<210> SEQ ID NO 2
<211> LENGTH: 361
<212> TYPE: PRT
<213> ORGANISM: Homo sapiens

<400> SEQUENCE: 2

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45
```

```
Leu Ala Leu Tyr Asn Ser Thr Arg Asp Arg Val Ala Gly Glu Ser Ala
             50                  55                  60

Glu Pro Glu Pro Glu Pro Glu Ala Asp Tyr Tyr Ala Lys Glu Val Thr
 65                  70                  75                  80

Arg Val Leu Met Val Glu Thr His Asn Glu Ile Tyr Asp Lys Phe Lys
                 85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
                180                 185                 190

His Cys Ser Cys Asp Ser Arg Asp Asn Thr Leu Gln Val Asp Ile Asn
                195                 200                 205

Gly Phe Thr Thr Gly Arg Arg Gly Asp Leu Ala Thr Ile His Gly Met
210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg Ala Leu Asp Thr Asn Tyr Cys
                245                 250                 255

Phe Ser Ser Thr Glu Lys Asn Cys Cys Val Arg Gln Leu Tyr Ile Asp
                260                 265                 270

Phe Arg Lys Asp Leu Gly Trp Lys Trp Ile His Glu Pro Lys Gly Tyr
            275                 280                 285

His Ala Asn Phe Cys Leu Gly Pro Cys Pro Tyr Ile Trp Ser Leu Asp
        290                 295                 300

Thr Gln Tyr Ser Lys Val Leu Ala Leu Tyr Asn Gln His Asn Pro Gly
305                 310                 315                 320

Ala Ser Ala Ala Pro Cys Cys Val Pro Gln Ala Leu Glu Pro Leu Pro
                325                 330                 335

Ile Val Tyr Tyr Val Gly Arg Lys Pro Lys Val Glu Gln Leu Ser Asn
                340                 345                 350

Met Ile Val Arg Ser Cys Lys Cys Ser
                355                 360

<210> SEQ ID NO 3
<211> LENGTH: 640
<212> TYPE: PRT
<213> ORGANISM: Homo sapiens

<400> SEQUENCE: 3

Glu Ile Asn Glu Cys Thr Val Asn Pro Asp Ile Cys Gly Ala Gly His
 1               5                  10                  15

Cys Ile Asn Leu Pro Val Arg Tyr Thr Cys Ile Cys Tyr Glu Gly Tyr
                 20                  25                  30

Arg Phe Ser Glu Gln Gln Arg Lys Cys Val Asp Ile Asp Glu Cys Thr
             35                  40                  45

Gln Val Gln His Leu Cys Ser Gln Gly Arg Cys Glu Asn Thr Glu Gly
```

```
            50                  55                  60
    Ser Phe Leu Cys Ile Cys Pro Ala Gly Phe Met Ala Ser Glu Glu Gly
    65                  70                  75                  80

Thr Asn Cys Ile Asp Val Asp Glu Cys Leu Arg Pro Asp Val Cys Gly
                        85                  90                  95

Glu Gly His Cys Val Asn Thr Val Gly Ala Phe Arg Cys Glu Tyr Cys
                100                 105                 110

Asp Ser Gly Tyr Arg Met Thr Gln Arg Gly Arg Cys Glu Asp Ile Asp
                115                 120                 125

Glu Cys Leu Asn Pro Ser Thr Cys Pro Asp Glu Gln Cys Val Asn Ser
        130                 135                 140

Pro Gly Ser Tyr Gln Cys Val Pro Cys Thr Glu Gly Phe Arg Gly Trp
    145                 150                 155                 160

Asn Gly Gln Cys Leu Asp Val Asp Glu Cys Leu Glu Pro Asn Val Cys
                        165                 170                 175

Ala Asn Gly Asp Cys Ser Asn Leu Glu Gly Ser Tyr Met Cys Ser Cys
                180                 185                 190

His Lys Gly Tyr Thr Arg Thr Pro Asp His Lys His Cys Arg Asp Ile
                195                 200                 205

Asp Glu Cys Gln Gln Gly Asn Leu Cys Val Asn Gly Gln Cys Lys Asn
        210                 215                 220

Thr Glu Gly Ser Phe Arg Cys Thr Cys Gly Gln Gly Tyr Gln Leu Ser
    225                 230                 235                 240

Ala Ala Lys Asp Gln Cys Glu Asp Ile Asp Glu Cys Gln His Arg His
                        245                 250                 255

Leu Cys Ala His Gly Gln Cys Arg Asn Thr Glu Gly Ser Phe Gln Cys
                260                 265                 270

Val Cys Asp Gln Gly Tyr Arg Ala Ser Gly Leu Gly Asp His Cys Glu
                275                 280                 285

Asp Ile Asn Glu Cys Leu Glu Asp Lys Ser Val Cys Gln Arg Gly Asp
        290                 295                 300

Cys Ile Asn Thr Ala Gly Ser Tyr Asp Cys Thr Cys Pro Asp Gly Phe
    305                 310                 315                 320

Gln Leu Asp Asp Asn Lys Thr Cys Gln Asp Ile Asn Glu Cys Glu His
                        325                 330                 335

Pro Gly Leu Cys Gly Pro Gln Gly Glu Cys Leu Asn Thr Glu Gly Ser
                340                 345                 350

Phe His Cys Val Cys Gln Gln Gly Phe Ser Ile Ser Ala Asp Gly Arg
                355                 360                 365

Thr Cys Glu Asp Ile Asp Glu Cys Val Asn Asn Thr Val Cys Asp Ser
        370                 375                 380

His Gly Phe Cys Asp Asn Thr Ala Gly Ser Phe Arg Cys Leu Cys Tyr
    385                 390                 395                 400

Gln Gly Phe Gln Ala Pro Gln Asp Gly Gln Gly Cys Val Asp Val Asn
                        405                 410                 415

Glu Cys Glu Leu Leu Ser Gly Val Cys Gly Glu Ala Phe Cys Glu Asn
                420                 425                 430

Val Glu Gly Ser Phe Leu Cys Val Cys Ala Asp Glu Asn Gln Glu Tyr
                435                 440                 445

Ser Pro Met Thr Gly Gln Cys Arg Ser Arg Thr Ser Thr Asp Leu Asp
        450                 455                 460

Val Asp Val Asp Gln Pro Lys Glu Glu Lys Lys Glu Cys Tyr Tyr Asn
    465                 470                 475                 480
```

```
Leu Asn Asp Ala Ser Leu Cys Asp Asn Val Leu Ala Pro Asn Val Thr
                485                 490                 495

Lys Gln Glu Cys Cys Thr Ser Gly Val Gly Trp Gly Asp Asn Cys
        500                 505                 510

Glu Ile Phe Pro Cys Pro Val Leu Gly Thr Ala Glu Phe Thr Glu Met
        515                 520                 525

Cys Pro Lys Gly Lys Gly Phe Val Pro Ala Gly Glu Ser Ser Ser Glu
        530                 535                 540

Ala Gly Gly Glu Asn Tyr Lys Asp Ala Asp Glu Cys Leu Leu Phe Gly
545                 550                 555                 560

Gln Glu Ile Cys Lys Asn Gly Phe Cys Leu Asn Thr Arg Pro Gly Tyr
                565                 570                 575

Glu Cys Tyr Cys Lys Gln Gly Thr Tyr Tyr Asp Pro Val Lys Leu Gln
                580                 585                 590

Cys Phe Asp Met Asp Glu Cys Gln Asp Pro Ser Ser Cys Ile Asp Gly
                595                 600                 605

Gln Cys Val Asn Thr Glu Gly Ser Tyr Asn Cys Phe Cys Thr His Pro
        610                 615                 620

Met Val Leu Asp Ala Ser Glu Lys Arg Cys Ile His His His His
625                 630                 635                 640

<210> SEQ ID NO 4
<211> LENGTH: 5
<212> TYPE: PRT
<213> ORGANISM: Homo sapiens

<400> SEQUENCE: 4

Asp Tyr Thr Met His
1               5

<210> SEQ ID NO 5
<211> LENGTH: 17
<212> TYPE: PRT
<213> ORGANISM: Homo sapiens

<400> SEQUENCE: 5

Leu Ile Ser Trp Asp Gly Gly Ser Thr Tyr Tyr Ala Asp Ser Val Lys
1               5                   10                  15

Gly

<210> SEQ ID NO 6
<211> LENGTH: 9
<212> TYPE: PRT
<213> ORGANISM: Homo sapiens

<400> SEQUENCE: 6

Asp Ala Asp Asp Ser Thr Phe Asp Ile
1               5

<210> SEQ ID NO 7
<211> LENGTH: 11
<212> TYPE: PRT
<213> ORGANISM: Homo sapiens

<400> SEQUENCE: 7

Arg Ala Ser Gln Ser Val Ser Arg Asn Leu Ala
1               5                   10

<210> SEQ ID NO 8
```

```
<211> LENGTH: 7
<212> TYPE: PRT
<213> ORGANISM: Homo sapiens

<400> SEQUENCE: 8

Trp Ala Ser Thr Arg Glu Ser
1               5

<210> SEQ ID NO 9
<211> LENGTH: 9
<212> TYPE: PRT
<213> ORGANISM: Homo sapiens

<400> SEQUENCE: 9

Gln Gln Tyr Tyr Ser Val Pro Tyr Thr
1               5

<210> SEQ ID NO 10
<211> LENGTH: 5
<212> TYPE: PRT
<213> ORGANISM: Homo sapiens

<400> SEQUENCE: 10

Ser Tyr Ala Ile Ser
1               5

<210> SEQ ID NO 11
<211> LENGTH: 17
<212> TYPE: PRT
<213> ORGANISM: Homo sapiens

<400> SEQUENCE: 11

Gly Ile Ile Pro Met Phe Gly Thr Thr Asn Tyr Ala Gln Lys Phe Gln
1               5                   10                  15

Gly

<210> SEQ ID NO 12
<211> LENGTH: 12
<212> TYPE: PRT
<213> ORGANISM: Homo sapiens

<400> SEQUENCE: 12

Asp Arg Glu Trp Glu Pro Ala Tyr Gly Met Asp Val
1               5                   10

<210> SEQ ID NO 13
<211> LENGTH: 14
<212> TYPE: PRT
<213> ORGANISM: Homo sapiens

<400> SEQUENCE: 13

Ile Gly Thr Ser Ser Asp Val Gly Gly Tyr Asn Tyr Val Ser
1               5                   10

<210> SEQ ID NO 14
<211> LENGTH: 7
<212> TYPE: PRT
<213> ORGANISM: Homo sapiens

<400> SEQUENCE: 14

Asp Val Ser Asn Arg Pro Ser
1               5

<210> SEQ ID NO 15
```

```
<211> LENGTH: 10
<212> TYPE: PRT
<213> ORGANISM: Homo sapiens

<400> SEQUENCE: 15

Ser Ala Tyr Thr Val Ser Ser Thr Trp Val
1               5                   10

<210> SEQ ID NO 16
<211> LENGTH: 444
<212> TYPE: PRT
<213> ORGANISM: Homo sapiens

<400> SEQUENCE: 16

Glu Val Gln Leu Val Gln Ser Gly Gly Val Val Gln Pro Gly Gly
1               5                   10                  15

Ser Leu Arg Leu Ser Cys Ala Ala Ser Gly Phe Thr Phe Asp Asp Tyr
                20                  25                  30

Thr Met His Trp Val Arg Gln Ala Pro Gly Lys Gly Leu Glu Trp Val
            35                  40                  45

Ser Leu Ile Ser Trp Asp Gly Gly Ser Thr Tyr Tyr Ala Asp Ser Val
        50                  55                  60

Lys Gly Arg Phe Thr Ile Ser Arg Asp Asn Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys Asp Ala Asp Asp Ser Thr Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335
```

```
Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
            435                 440
```

<210> SEQ ID NO 17
<211> LENGTH: 214
<212> TYPE: PRT
<213> ORGANISM: Homo sapiens

<400> SEQUENCE: 17

```
Glu Thr Thr Leu Thr Gln Ser Pro Ala Thr Leu Ser Val Ser Pro Gly
1               5                   10                  15

Glu Arg Val Thr Leu Ser Cys Arg Ala Ser Gln Ser Val Ser Arg Asn
            20                  25                  30

Leu Ala Trp Tyr Gln Gln Lys Pro Gly Gln Pro Pro Lys Leu Leu Ile
        35                  40                  45

Tyr Trp Ala Ser Thr Arg Glu Ser Gly Val Pro Asp Arg Phe Ser Gly
50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Tyr Tyr Ser Val Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 18
<211> LENGTH: 447
<212> TYPE: PRT
<213> ORGANISM: Homo sapiens

<400> SEQUENCE: 18

```
Gln Met Gln Leu Val Gln Ser Gly Ala Glu Lys Lys Pro Gly Ser
1               5                   10                  15

Ser Val Lys Val Ser Cys Lys Ala Ser Gly Gly Thr Phe Ser Ser Tyr
        20                  25                  30

Ala Ile Ser Trp Val Arg Gln Ala Pro Gly Gln Gly Leu Glu Trp Met
        35                  40                  45

Gly Gly Ile Ile Pro Met Phe Gly Thr Thr Asn Tyr Ala Gln Lys Phe
    50                  55                  60

Gln Gly Arg Val Thr Ile Ile Ala Asp Glu Ser Thr Ser Thr Ala Tyr
65              70                  75                  80

Met Glu Leu Arg Ser Leu Arg Ser Asp Asp Thr Ala Val Tyr Tyr Cys
                85                  90                  95

Ala Arg Asp Arg Glu Trp Glu Pro Ala Tyr Gly Met Asp Val Trp Gly
                100                 105                 110

Gln Gly Thr Thr Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415
```

```
Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly
            435                 440                 445

<210> SEQ ID NO 19
<211> LENGTH: 216
<212> TYPE: PRT
<213> ORGANISM: Homo sapiens

<400> SEQUENCE: 19

Gln Ser Ala Leu Thr Gln Pro Ala Ser Val Ser Gly Ser Pro Gly Gln
1               5                   10                  15

Ser Ile Thr Ile Ser Cys Ile Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Ala Met Tyr Tyr Cys Ser Ala Tyr Thr Val Ser
            85                  90                  95

Ser Thr Trp Val Phe Gly Gly Gly Thr Lys Val Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
            165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```